United States Patent
Reiley et al.

(10) Patent No.: US 9,056,016 B2
(45) Date of Patent: Jun. 16, 2015

(54) POLYAXIAL ADJUSTMENT OF FACET JOINT PROSTHESES

(75) Inventors: Mark A. Reiley, Piedmont, CA (US); David T. Stinson, Woodinville, WA (US); Robert M. Scribner, Boulder, CO (US); Leonard J. Tokish, Jr., Issaquah, WA (US)

(73) Assignee: GMEDELAWARE 2 LLC, Audubon, PA (US)

( * ) Notice: Subject to any disclaimer, the term of this patent is extended or adjusted under 35 U.S.C. 154(b) by 1032 days.

(21) Appl. No.: 12/058,403

(22) Filed: Mar. 28, 2008

(65) Prior Publication Data

US 2008/0177332 A1 Jul. 24, 2008

Related U.S. Application Data

(63) Continuation of application No. 10/737,705, filed on Dec. 15, 2003, now abandoned.

(51) Int. Cl.
*A61B 17/70* (2006.01)
*A61F 2/44* (2006.01)
(Continued)

(52) U.S. Cl.
CPC ............ *A61F 2/4405* (2013.01); *A61B 17/7064* (2013.01); *A61B 17/86* (2013.01); *A61F 2002/30365* (2013.01); *A61F 2002/30367* (2013.01); *A61F 2002/30373* (2013.01); *A61F 2002/30375* (2013.01);
(Continued)

(58) Field of Classification Search
CPC ............ A61B 17/7062; A61B 17/7041; A61F 2002/30616
USPC ............... 606/246–279; 623/17.11, 17.13, 61
See application file for complete search history.

(56) References Cited

U.S. PATENT DOCUMENTS

| 1,308,451 A | 7/1919 | Schachat |
| 2,502,902 A | 4/1950 | Tofflemire |

(Continued)

FOREIGN PATENT DOCUMENTS

| DE | 10135771 A1 | 7/2001 |
| DE | 10312755 A1 | 10/2003 |

(Continued)

OTHER PUBLICATIONS

Ochoa et al.; U.S. Appl. No. 12/377,546 entitled "Spinal implant," filed Feb. 13, 2009.

(Continued)

*Primary Examiner* — Jan Christopher Merene
*Assistant Examiner* — Atiya Mahmud

(57) ABSTRACT

Prostheses, systems, and methods are provided for replacement of natural facet joints between adjacent vertebrae using polyaxial attachment mechanisms for securing the prostheses to the vertebrae. A cephalad prosthesis attached to a superior adjacent vertebra replaces the inferior half of a natural facet joint. A caudal prosthesis attached to an inferior adjacent vertebra replaces the superior half of a natural facet joint. Both the cephalad and caudal prostheses are configured with artificial facet joint structures that include articulating surfaces that cooperate and form an artificial articular configuration. The polyaxial attachment mechanism permits adjustment of the position of the artificial facet joint structure along more than one axis at or after the time the cephalad or caudal prosthesis is attached to a vertebra.

9 Claims, 15 Drawing Sheets

(51) Int. Cl.
*A61B 17/86* (2006.01)
*A61F 2/30* (2006.01)
*A61F 2/46* (2006.01)

(52) U.S. Cl.
CPC ............... *A61F 2002/30438* (2013.01); *A61F 2002/30443* (2013.01); *A61F 2002/30507* (2013.01); *A61F 2002/30512* (2013.01); *A61F 2002/30538* (2013.01); *A61F 2002/3055* (2013.01); *A61F 2002/30553* (2013.01); *A61F 2002/30604* (2013.01); *A61F 2002/30616* (2013.01); *A61F 2002/30649* (2013.01); *A61F 2002/4631* (2013.01); *A61F 2220/0025* (2013.01); *A61F 2220/0033* (2013.01); *A61F 2220/0041* (2013.01); *A61F 2250/0006* (2013.01); *A61F 2250/0007* (2013.01); *A61F 2250/0008* (2013.01); *A61F 2310/00017* (2013.01); *A61F 2310/00023* (2013.01); *A61F 2310/00029* (2013.01); *A61F 2310/00047* (2013.01); *A61F 2310/00131* (2013.01); *A61F 2310/00179* (2013.01)

(56) References Cited

U.S. PATENT DOCUMENTS

| | | | |
|---|---|---|---|
| 2,930,133 A | 3/1960 | Thompson |
| 2,959,861 A | 11/1960 | Stromquist |
| 3,596,656 A | 8/1971 | Kaute |
| 3,710,789 A | 1/1973 | Ersek |
| 3,726,279 A | 4/1973 | Barefoot et al. |
| 3,867,728 A | 2/1975 | Stubstad et al. |
| 3,875,595 A | 4/1975 | Froning |
| 3,941,127 A | 3/1976 | Froning |
| 4,040,130 A | 8/1977 | Laure |
| 4,123,848 A | 11/1978 | Emmerich et al. |
| 4,156,296 A | 5/1979 | Johnson et al. |
| 4,210,317 A | 7/1980 | Spann et al. |
| 4,231,121 A | 11/1980 | Lewis |
| 4,271,836 A | 6/1981 | Bacal et al. |
| 4,349,921 A | 9/1982 | Kuntz |
| 4,394,370 A | 7/1983 | Jefferies |
| 4,472,840 A | 9/1984 | Jefferies |
| 4,502,161 A | 3/1985 | Wall |
| 4,554,914 A | 11/1985 | Kapp et al. |
| 4,611,581 A | 9/1986 | Steffee |
| 4,633,722 A | 1/1987 | Beardmore et al. |
| 4,693,722 A | 9/1987 | Wall |
| 4,697,582 A | 10/1987 | William |
| 4,710,075 A | 12/1987 | Davison |
| 4,759,769 A | 7/1988 | Hedman et al. |
| 4,772,287 A | 9/1988 | Ray et al. |
| 4,778,472 A | 10/1988 | Homsy et al. |
| 4,795,469 A | 1/1989 | Oh |
| 4,805,602 A | 2/1989 | Puno et al. |
| 4,863,477 A | 9/1989 | Monson |
| 4,904,260 A | 2/1990 | Ray et al. |
| 4,911,718 A | 3/1990 | Lee et al. |
| 4,917,701 A | 4/1990 | Morgan |
| 4,932,975 A | 6/1990 | Main et al. |
| 4,950,270 A | 8/1990 | Bowman et al. |
| 4,955,916 A | 9/1990 | Carignan et al. |
| 4,957,495 A | 9/1990 | Kluger |
| 4,987,904 A | 1/1991 | Wilson |
| 5,000,165 A | 3/1991 | Watanabe |
| 5,015,255 A | 5/1991 | Kuslich |
| 5,019,081 A | 5/1991 | Watanabe |
| 5,047,055 A | 9/1991 | Bao et al. |
| 5,062,845 A | 11/1991 | Kuslich et al. |
| 5,070,623 A | 12/1991 | Barnes |
| 5,071,437 A | 12/1991 | Steffee |
| 5,092,866 A | 3/1992 | Breard et al. |
| 5,098,434 A | 3/1992 | Serbousek |
| 5,108,399 A | 4/1992 | Eitenmuller et al. |
| 5,129,900 A | 7/1992 | Asher et al. |
| 5,147,404 A | 9/1992 | Downey |
| 5,171,280 A | 12/1992 | Baumgartner |
| 5,192,326 A | 3/1993 | Bao et al. |
| 5,258,031 A | 11/1993 | Salib et al. |
| 5,261,910 A | 11/1993 | Warden et al. |
| 5,284,655 A | 2/1994 | Bogdansky et al. |
| 5,300,073 A | 4/1994 | Ray et al. |
| 5,303,480 A | 4/1994 | Chek |
| 5,306,308 A | 4/1994 | Gross et al. |
| 5,306,309 A | 4/1994 | Wagner et al. |
| 5,312,409 A | 5/1994 | McLaughlin et al. |
| 5,314,429 A | 5/1994 | Goble |
| 5,314,476 A | 5/1994 | Prewett et al. |
| 5,314,486 A | 5/1994 | Zang et al. |
| 5,314,489 A | 5/1994 | Hoffman et al. |
| 5,314,492 A | 5/1994 | Hamilton et al. |
| 5,329,933 A | 7/1994 | Graf |
| 5,334,203 A | 8/1994 | Wagner |
| 5,348,026 A | 9/1994 | Davidson |
| 5,350,380 A | 9/1994 | Goble et al. |
| 5,360,448 A | 11/1994 | Thramann |
| 5,370,697 A | 12/1994 | Baumgartner |
| 5,401,269 A | 3/1995 | Buttner-Janz et al. |
| 5,405,390 A | 4/1995 | O'Leary et al. |
| 5,413,576 A | 5/1995 | Rivard |
| 5,415,659 A | 5/1995 | Lee et al. |
| 5,415,661 A | 5/1995 | Holmes |
| 5,425,773 A | 6/1995 | Boyd et al. |
| 5,437,669 A | 8/1995 | Yuan et al. |
| 5,437,672 A | 8/1995 | Alleyne |
| 5,443,483 A | 8/1995 | Kirsch |
| 5,445,639 A | 8/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,470,333 A | 11/1995 | Ray |
| 5,474,551 A * | 12/1995 | Finn et al. ............... 606/264 |
| 5,474,555 A | 12/1995 | Puno et al. |
| 5,491,882 A | 2/1996 | Walston et al. |
| 5,496,318 A | 3/1996 | Howland et al. |
| 5,501,684 A | 3/1996 | Schlapfer et al. |
| 5,507,823 A | 4/1996 | Walston et al. |
| 5,510,396 A | 4/1996 | Prewett et al. |
| 5,514,180 A | 5/1996 | Heggeness et al. |
| 5,527,312 A | 6/1996 | Ray |
| 5,534,028 A | 7/1996 | Bao et al. |
| 5,534,030 A | 7/1996 | Navarro et al. |
| 5,545,229 A | 8/1996 | Parsons et al. |
| 5,556,431 A | 9/1996 | Buttner-Janz |
| 5,562,737 A * | 10/1996 | Graf ....................... 623/17.14 |
| 5,562,738 A | 10/1996 | Boyd et al. |
| 5,569,247 A | 10/1996 | Morrison |
| 5,571,189 A | 11/1996 | Kuslich |
| 5,571,191 A | 11/1996 | Fitz |
| 5,575,792 A | 11/1996 | Errico et al. |
| 5,577,995 A | 11/1996 | Walker et al. |
| 5,587,695 A | 12/1996 | Warmerdam |
| 5,599,311 A | 2/1997 | Raulerson |
| 5,603,713 A | 2/1997 | Aust et al. |
| 5,609,641 A | 3/1997 | Johnson et al. |
| 5,643,263 A | 7/1997 | Simonson |
| 5,645,597 A | 7/1997 | Krapiva |
| 5,645,599 A | 7/1997 | Samani |
| 5,649,930 A | 7/1997 | Kertzner |
| 5,653,762 A | 8/1997 | Pisharodi |
| 5,658,338 A | 8/1997 | Tullos et al. |
| 5,662,651 A | 9/1997 | Tornier et al. |
| 5,672,175 A | 9/1997 | Martin |
| 5,674,295 A | 10/1997 | Ray et al. |
| 5,674,296 A | 10/1997 | Bryan et al. |
| 5,676,701 A | 10/1997 | Yuan et al. |
| 5,678,317 A | 10/1997 | Stefanakos |
| 5,683,391 A | 11/1997 | Boyd |
| 5,683,392 A | 11/1997 | Richelsoph et al. |
| 5,683,464 A | 11/1997 | Wagner et al. |
| 5,683,466 A | 11/1997 | Vitale |
| 5,688,274 A | 11/1997 | Errico et al. |
| 5,690,630 A | 11/1997 | Errico et al. |

(56) References Cited

U.S. PATENT DOCUMENTS

| | | |
|---|---|---|
| 5,700,268 A | 12/1997 | Bertin |
| 5,702,450 A | 12/1997 | Bisserie |
| 5,704,941 A | 1/1998 | Jacober et al. |
| 5,716,415 A | 2/1998 | Steffee |
| 5,725,527 A | 3/1998 | Biedermann et al. |
| 5,733,284 A | 3/1998 | Martin |
| 5,738,585 A | 4/1998 | Hoyt, III et al. |
| 5,741,255 A | 4/1998 | Krag et al. |
| 5,741,261 A | 4/1998 | Moskovitz et al. |
| 5,766,253 A | 6/1998 | Brosnahan, III |
| 5,776,135 A | 7/1998 | Errico et al. |
| 5,782,833 A | 7/1998 | Haider |
| 5,797,911 A | 8/1998 | Sherman et al. |
| 5,800,433 A | 9/1998 | Benzel et al. |
| 5,824,093 A | 10/1998 | Ray et al. |
| 5,824,094 A | 10/1998 | Serhan et al. |
| 5,827,289 A | 10/1998 | Reiley et al. |
| 5,836,948 A | 11/1998 | Zucherman et al. |
| 5,860,977 A | 1/1999 | Zucherman et al. |
| 5,863,293 A | 1/1999 | Richelsoph |
| 5,865,846 A | 2/1999 | Bryan et al. |
| 5,866,113 A | 2/1999 | Hoensbroek et al. |
| 5,868,745 A | 2/1999 | Alleyne |
| 5,879,350 A | 3/1999 | Sherman et al. |
| 5,879,396 A | 3/1999 | Walston et al. |
| 5,885,285 A | 3/1999 | Simonson |
| 5,885,286 A | 3/1999 | Sherman et al. |
| 5,891,145 A | 4/1999 | Morrison et al. |
| 5,893,889 A * | 4/1999 | Harrington ............... 623/17.16 |
| RE36,221 E | 6/1999 | Breard et al. |
| 5,947,893 A | 9/1999 | Agrawal et al. |
| 5,947,965 A | 9/1999 | Bryan |
| 5,964,760 A | 10/1999 | Richelsoph |
| 5,984,926 A | 11/1999 | Jones |
| 6,001,130 A | 12/1999 | Bryan et al. |
| 6,004,353 A | 12/1999 | Masini |
| 6,010,503 A | 1/2000 | Richelsoph et al. |
| 6,014,588 A | 1/2000 | Fitz |
| 6,019,759 A | 2/2000 | Rogozinski |
| 6,019,792 A | 2/2000 | Cauthen |
| 6,022,350 A | 2/2000 | Ganem |
| 6,039,763 A | 3/2000 | Shelokov |
| 6,048,342 A | 4/2000 | Zucherman et al. |
| 6,050,997 A * | 4/2000 | Mullane ...................... 606/250 |
| 6,053,917 A | 4/2000 | Sherman et al. |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,074,391 A | 6/2000 | Metz-Stavenhagen et al. |
| 6,077,262 A | 6/2000 | Schläpfer et al. |
| 6,080,157 A | 6/2000 | Cathro et al. |
| 6,086,590 A | 7/2000 | Margulies et al. |
| 6,090,111 A | 7/2000 | Nichols |
| 6,113,600 A | 9/2000 | Drummond et al. |
| 6,113,637 A | 9/2000 | Gill et al. |
| 6,120,510 A | 9/2000 | Albrektsson et al. |
| 6,132,430 A | 10/2000 | Wagner |
| 6,132,462 A | 10/2000 | Li |
| 6,132,464 A * | 10/2000 | Martin ...................... 623/17.15 |
| 6,132,465 A | 10/2000 | Ray et al. |
| 6,165,177 A | 12/2000 | Wilson et al. |
| 6,190,388 B1 | 2/2001 | Michelson et al. |
| 6,193,724 B1 | 2/2001 | Chan |
| 6,193,758 B1 | 2/2001 | Huebner |
| 6,200,322 B1 | 3/2001 | Branch et al. |
| 6,214,012 B1 | 4/2001 | Karpman et al. |
| 6,224,602 B1 | 5/2001 | Hayes |
| 6,231,575 B1 | 5/2001 | Krag |
| 6,241,730 B1 * | 6/2001 | Alby ............................ 606/256 |
| 6,248,105 B1 | 6/2001 | Schläpfer et al. |
| 6,280,443 B1 | 8/2001 | Gu et al. |
| 6,290,703 B1 | 9/2001 | Ganem |
| 6,293,949 B1 | 9/2001 | Justis et al. |
| 6,302,890 B1 | 10/2001 | Leone, Jr. |
| 6,309,391 B1 | 10/2001 | Crandall et al. |
| 6,312,431 B1 | 11/2001 | Asfora |
| 6,340,361 B1 | 1/2002 | Kraus et al. |
| 6,340,477 B1 | 1/2002 | Anderson |
| 6,342,054 B1 | 1/2002 | Mata |
| 6,361,506 B1 | 3/2002 | Saenger et al. |
| 6,368,320 B1 | 4/2002 | Le Couedic et al. |
| 6,419,703 B1 | 7/2002 | Fallin et al. |
| 6,440,169 B1 | 8/2002 | Elberg et al. |
| 6,443,954 B1 | 9/2002 | Bramlet et al. |
| 6,451,021 B1 | 9/2002 | Ralph et al. |
| 6,471,705 B1 | 10/2002 | Biedermann et al. |
| 6,514,253 B1 | 2/2003 | Yao |
| 6,520,963 B1 | 2/2003 | McKinley |
| 6,524,315 B1 | 2/2003 | Selvitelli et al. |
| 6,540,749 B2 | 4/2003 | Schäfer et al. |
| 6,547,790 B2 | 4/2003 | Harkey, III et al. |
| 6,554,831 B1 * | 4/2003 | Rivard et al. ................. 606/253 |
| 6,554,843 B1 | 4/2003 | Ou |
| 6,565,565 B1 | 5/2003 | Yuan et al. |
| 6,565,572 B2 | 5/2003 | Chappius |
| 6,565,605 B2 | 5/2003 | Goble et al. |
| 6,572,617 B1 | 6/2003 | Senegas |
| 6,579,319 B2 * | 6/2003 | Goble et al. ............... 623/17.11 |
| 6,585,740 B2 | 7/2003 | Schlapfer et al. |
| 6,585,769 B1 | 7/2003 | Muhanna et al. |
| 6,607,530 B1 | 8/2003 | Carl et al. |
| 6,610,091 B1 | 8/2003 | Reiley |
| 6,619,091 B2 | 9/2003 | Heffe |
| 6,620,164 B2 * | 9/2003 | Ueyama et al. ............... 606/261 |
| 6,623,485 B2 * | 9/2003 | Doubler et al. ............... 606/301 |
| 6,626,909 B2 | 9/2003 | Chin |
| 6,632,226 B2 | 10/2003 | Chan |
| 6,638,281 B2 | 10/2003 | Gorek |
| 6,645,214 B2 | 11/2003 | Brown et al. |
| 6,648,891 B2 | 11/2003 | Kim |
| 6,669,698 B1 | 12/2003 | Tromanhauser et al. |
| 6,669,729 B2 | 12/2003 | Chin |
| 6,676,661 B1 * | 1/2004 | Martin Benlloch et al. .. 606/264 |
| 6,712,818 B1 | 3/2004 | Michelson |
| 6,712,849 B2 | 3/2004 | Re et al. |
| 6,736,815 B2 | 5/2004 | Ginn |
| 6,749,361 B2 | 6/2004 | Hermann et al. |
| 6,761,698 B2 | 7/2004 | Shibata et al. |
| 6,761,720 B1 | 7/2004 | Senegas |
| 6,770,095 B2 | 8/2004 | Grinberg et al. |
| 6,783,527 B2 | 8/2004 | Drewry et al. |
| 6,790,233 B2 | 9/2004 | Brodke et al. |
| 6,802,844 B2 * | 10/2004 | Ferree ......................... 606/258 |
| 6,811,567 B2 * | 11/2004 | Reiley ...................... 623/17.11 |
| 6,902,567 B2 | 6/2005 | Del Medico |
| 6,902,580 B2 | 6/2005 | Fallin et al. |
| 6,908,465 B2 | 6/2005 | von Hoffmann et al. |
| 6,949,123 B2 | 9/2005 | Reiley |
| 6,974,478 B2 | 12/2005 | Reiley et al. |
| 6,979,299 B2 | 12/2005 | Peabody et al. |
| 7,011,658 B2 | 3/2006 | Young |
| 7,044,969 B2 | 5/2006 | Errico et al. |
| 7,051,451 B2 * | 5/2006 | Augostino et al. ............... 33/512 |
| 7,074,238 B2 * | 7/2006 | Stinson et al. ............. 623/17.11 |
| 7,083,621 B2 * | 8/2006 | Shaolian et al. ............ 606/86 A |
| 7,220,262 B1 | 5/2007 | Hynes |
| 7,294,127 B2 | 11/2007 | Leung et al. |
| 7,302,288 B1 | 11/2007 | Schellenberg |
| 7,309,338 B2 | 12/2007 | Cragg |
| 7,445,635 B2 | 11/2008 | Fallin et al. |
| 7,455,685 B2 | 11/2008 | Justis |
| 7,547,324 B2 | 6/2009 | Cragg et al. |
| 7,708,764 B2 * | 5/2010 | Simonson ..................... 606/279 |
| 7,727,258 B2 * | 6/2010 | Graf ............................ 606/253 |
| 7,862,586 B2 * | 1/2011 | Malek .......................... 606/246 |
| 2001/0012938 A1 | 8/2001 | Zucherman et al. |
| 2001/0020170 A1 | 9/2001 | Zucherman et al. |
| 2002/0013585 A1 | 1/2002 | Gournay et al. |
| 2002/0013588 A1 | 1/2002 | Landry et al. |
| 2002/0029039 A1 | 3/2002 | Zucherman et al. |
| 2002/0042613 A1 | 4/2002 | Mata |
| 2002/0052603 A1 * | 5/2002 | Nichols et al. ................. 606/61 |
| 2002/0068975 A1 | 6/2002 | Teitelbaum et al. |

(56) References Cited

U.S. PATENT DOCUMENTS

| | | |
|---|---|---|
| 2002/0082601 A1 | 6/2002 | Toyama et al. |
| 2002/0120272 A1 | 8/2002 | Yuan et al. |
| 2002/0123752 A1 | 9/2002 | Schultheiss et al. |
| 2002/0151895 A1 | 10/2002 | Soboleski et al. |
| 2003/0004572 A1 | 1/2003 | Goble et al. |
| 2003/0055427 A1* | 3/2003 | Graf ................ 606/61 |
| 2003/0069603 A1 | 4/2003 | Little et al. |
| 2003/0125740 A1 | 7/2003 | Khanna |
| 2003/0181914 A1 | 9/2003 | Johnson et al. |
| 2003/0191532 A1 | 10/2003 | Goble et al. |
| 2003/0195631 A1 | 10/2003 | Ferree |
| 2003/0204259 A1 | 10/2003 | Goble et al. |
| 2003/0204261 A1 | 10/2003 | Eisermann et al. |
| 2003/0229345 A1* | 12/2003 | Stahurski ................ 606/61 |
| 2003/0233148 A1 | 12/2003 | Ferree |
| 2004/0006391 A1 | 1/2004 | Reiley |
| 2004/0049205 A1 | 3/2004 | Lee et al. |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0092931 A1* | 5/2004 | Taylor et al. ................ 606/61 |
| 2004/0111154 A1 | 6/2004 | Reiley |
| 2004/0116927 A1 | 6/2004 | Graf |
| 2004/0127989 A1 | 7/2004 | Dooris et al. |
| 2004/0143264 A1 | 7/2004 | McAfee |
| 2004/0204710 A1 | 10/2004 | Patel et al. |
| 2004/0204718 A1 | 10/2004 | Hoffman |
| 2004/0210216 A1* | 10/2004 | Farris et al. ................ 606/61 |
| 2004/0230201 A1 | 11/2004 | Yuan et al. |
| 2004/0230304 A1 | 11/2004 | Yuan et al. |
| 2004/0254574 A1* | 12/2004 | Morrison et al. ................ 606/61 |
| 2004/0260305 A1 | 12/2004 | Gorensek et al. |
| 2005/0010291 A1 | 1/2005 | Stinson et al. |
| 2005/0015146 A1 | 1/2005 | Louis et al. |
| 2005/0027359 A1 | 2/2005 | Mashburn |
| 2005/0027361 A1 | 2/2005 | Reiley |
| 2005/0033431 A1 | 2/2005 | Gordon et al. |
| 2005/0033432 A1 | 2/2005 | Gordon et al. |
| 2005/0033434 A1* | 2/2005 | Berry ................ 623/17.14 |
| 2005/0033439 A1 | 2/2005 | Gordon et al. |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0059972 A1 | 3/2005 | Biscup |
| 2005/0080428 A1 | 4/2005 | White |
| 2005/0080486 A1 | 4/2005 | Fallin et al. |
| 2005/0085912 A1 | 4/2005 | Arnin et al. |
| 2005/0090823 A1* | 4/2005 | Bartimus ................ 606/61 |
| 2005/0101956 A1 | 5/2005 | Simonson |
| 2005/0102028 A1 | 5/2005 | Arnin et al. |
| 2005/0113927 A1* | 5/2005 | Malek ................ 623/17.16 |
| 2005/0119748 A1 | 6/2005 | Reiley et al. |
| 2005/0131405 A1* | 6/2005 | Molz et al. ................ 606/61 |
| 2005/0131406 A1 | 6/2005 | Reiley et al. |
| 2005/0137705 A1 | 6/2005 | Reiley |
| 2005/0137706 A1 | 6/2005 | Reiley |
| 2005/0143818 A1 | 6/2005 | Yuan et al. |
| 2005/0149190 A1 | 7/2005 | Reiley |
| 2005/0228500 A1 | 10/2005 | Kim et al. |
| 2005/0234552 A1 | 10/2005 | Reiley |
| 2005/0240264 A1 | 10/2005 | Tokish, Jr. et al. |
| 2005/0240265 A1 | 10/2005 | Kuiper et al. |
| 2005/0240266 A1 | 10/2005 | Kuiper et al. |
| 2005/0251256 A1 | 11/2005 | Reiley |
| 2005/0261770 A1 | 11/2005 | Kuiper et al. |
| 2005/0267579 A1 | 12/2005 | Reiley et al. |
| 2005/0283238 A1 | 12/2005 | Reiley |
| 2006/0009847 A1 | 1/2006 | Reiley |
| 2006/0009848 A1 | 1/2006 | Reiley |
| 2006/0009849 A1 | 1/2006 | Reiley |
| 2006/0029186 A1 | 2/2006 | De Villiers et al. |
| 2006/0041311 A1 | 2/2006 | McLeer |
| 2006/0052785 A1 | 3/2006 | Augostino et al. |
| 2006/0058791 A1 | 3/2006 | Broman et al. |
| 2006/0079895 A1 | 4/2006 | McLeer |
| 2006/0085072 A1 | 4/2006 | Funk et al. |
| 2006/0085075 A1 | 4/2006 | McLeer |
| 2006/0100707 A1 | 5/2006 | Stinson et al. |
| 2006/0100709 A1 | 5/2006 | Reiley |
| 2006/0122703 A1 | 6/2006 | Aebi et al. |
| 2006/0149375 A1 | 7/2006 | Yuan et al. |
| 2006/0184180 A1 | 8/2006 | Augostino et al. |
| 2006/0265070 A1 | 11/2006 | Stinson et al. |
| 2007/0079517 A1 | 4/2007 | Augostino et al. |
| 2007/0088358 A1 | 4/2007 | Yuan et al. |
| 2007/0093833 A1 | 4/2007 | Kuiper et al. |
| 2007/0168029 A1 | 7/2007 | Yuan et al. |
| 2007/0233256 A1 | 10/2007 | Ohrt et al. |
| 2007/0255411 A1 | 11/2007 | Reiley |
| 2007/0265706 A1 | 11/2007 | Reiley |
| 2007/0276374 A1 | 11/2007 | Broman et al. |
| 2007/0282445 A1 | 12/2007 | Reiley |
| 2008/0015583 A1 | 1/2008 | Reiley |
| 2008/0015585 A1 | 1/2008 | Berg et al. |
| 2008/0015696 A1 | 1/2008 | Reiley |
| 2008/0045954 A1 | 2/2008 | Reiley et al. |
| 2008/0082171 A1 | 4/2008 | Kuiper et al. |
| 2008/0086213 A1 | 4/2008 | Reiley |
| 2008/0091200 A1 | 4/2008 | Kuiper et al. |
| 2008/0091201 A1 | 4/2008 | Reiley |
| 2008/0091202 A1 | 4/2008 | Reiley |
| 2008/0091204 A1 | 4/2008 | Kuiper et al. |
| 2008/0091205 A1 | 4/2008 | Kuiper et al. |
| 2008/0091210 A1 | 4/2008 | Reiley |
| 2008/0091268 A1 | 4/2008 | Reiley |
| 2008/0097437 A1 | 4/2008 | Reiley |
| 2008/0097438 A1 | 4/2008 | Reiley |
| 2008/0097439 A1 | 4/2008 | Reiley |
| 2008/0097440 A1 | 4/2008 | Reiley et al. |
| 2008/0097446 A1 | 4/2008 | Reiley et al. |
| 2008/0097609 A1 | 4/2008 | Reiley |
| 2008/0097612 A1 | 4/2008 | Reiley |
| 2008/0097613 A1 | 4/2008 | Reiley et al. |
| 2008/0103501 A1 | 5/2008 | Ralph et al. |
| 2008/0119845 A1 | 5/2008 | Stone et al. |
| 2008/0125814 A1 | 5/2008 | Yuan et al. |
| 2008/0132951 A1 | 6/2008 | Reiley et al. |
| 2008/0140121 A1 | 6/2008 | McLeer |
| 2008/0177308 A1 | 7/2008 | McLeer |
| 2008/0177309 A1 | 7/2008 | McLeer |
| 2008/0177310 A1 | 7/2008 | Reiley |
| 2008/0177332 A1 | 7/2008 | Reiley et al. |
| 2008/0200953 A1 | 8/2008 | Reiley et al. |
| 2008/0249568 A1 | 10/2008 | Kuiper et al. |

FOREIGN PATENT DOCUMENTS

| | | |
|---|---|---|
| EP | 1103226 | 5/2001 |
| EP | 1205152 A1 | 5/2002 |
| EP | 1254639 A1 | 11/2002 |
| FR | 2726459 | 5/1996 |
| FR | 2749155 | 12/1997 |
| FR | 2844180 | 3/2004 |
| IE | S970323 | 6/1998 |
| JP | 59010807 A | 1/1984 |
| JP | 10082605 A | 3/1998 |
| JP | 10179622 A | 7/1998 |
| WO | WO 95/05783 A1 | 3/1995 |
| WO | WO 96/00049 A1 | 1/1996 |
| WO | WO 98/48717 A1 | 11/1998 |
| WO | WO 98/56301 A1 | 12/1998 |
| WO | WO 99/05995 A1 | 2/1999 |
| WO | WO 99/23963 A1 | 5/1999 |
| WO | WO 99/60957 A1 | 12/1999 |
| WO | WO 99/65412 A1 | 12/1999 |
| WO | WO 00/38582 A1 | 7/2000 |
| WO | WO 00/62684 A1 | 10/2000 |
| WO | WO 01/06939 A1 | 2/2001 |
| WO | WO 01/15638 A1 | 3/2001 |

(56) References Cited

FOREIGN PATENT DOCUMENTS

| WO | WO 01/28442 A1 | 4/2001 |
|---|---|---|
| WO | WO 01/30248 A1 | 5/2001 |
| WO | WO 01/39678 A1 | 6/2001 |
| WO | WO 01/67972 A2 | 9/2001 |
| WO | WO 01/97721 A2 | 12/2001 |
| WO | WO 02/00270 A1 | 1/2002 |
| WO | WO 02/00275 A1 | 1/2002 |
| WO | WO 02/02024 A1 | 1/2002 |
| WO | WO 02/02158 A1 | 1/2002 |
| WO | WO 02/34150 A2 | 5/2002 |
| WO | WO 02/43603 A1 | 6/2002 |
| WO | WO 02/071960 A1 | 9/2002 |
| WO | WO 02/089712 A1 | 11/2002 |
| WO | WO 03/020143 A1 | 3/2003 |
| WO | WO 03/041618 A2 | 5/2003 |
| WO | WO 03/075805 A1 | 9/2003 |
| WO | WO 03/101350 A1 | 12/2003 |
| WO | WO 2004/071358 A1 | 8/2004 |
| WO | WO 2004/103227 A1 | 12/2004 |
| WO | WO 2004/103228 A1 | 12/2004 |
| WO | WO 2005/009301 A1 | 2/2005 |

OTHER PUBLICATIONS

Hewko, Brian; U.S. Appl. No. 12/377,552 entitled "Spinal implant," filed Feb. 13, 2009.

Kuiper et al.; U.S. Appl. No. 11/577,967 entitled "Crossbar Spinal Prosthesis having a Modular Design and Systems for Treating Spinal Pathologies," filed Apr. 25, 2007.

McLeer, Thomas, U.S. Appl. No. 11/934,719 entitled "Polymeric Joint Complex and Methods of Use" filed Nov. 2, 2007.

Quest et al.; U.S. Appl. No. 12/099,068 entitled "Measurement and trialing system and methods for orthopedic device component selection," filed Apr. 7, 2008.

Reiley, Mark; U.S. Appl. No. 12/176,280 entitled "Facet arthroplasty devices and methods," filed Jul. 18, 2008.

Yuan et al.; U.S. Appl. No. 12/163,738 entitled "Prostheses, tools and methods for replacement of natural joints with artificial facet joint surfaces," filed Aug. 5, 2008.

Funk et al.; U.S. Appl. No. 12/186,461 entitled "Implantable orthopedic device component selection instrument and methods," filed Aug. 5, 2008.

Abraham, D.J. et al. "Indications and Trends in Use in Cervical Spinal Fusions." Orthop Clin North Am. Oct. 1998; 29(4):731-44.

Eichholz, K.M. et al. "Complications of Revision Spinal Surgery", Neurosurg Focus; (Sep. 15, 2003), 15(3): pp. 1-4.

Farfan, H.F. "Effects of Torsion on the Intervertebral Joints." The Canadian Journal of Surgery, Jul. 1969; 12(3):336-41.

Farfan, H.F. et al. "The Relation of Facet Orientation to Intervertebral Disc Failure." The Canadian Journal of Surgery, Apr. 1967; 10(2):179-85.

Farfan, H.F. The Pathological Anatomy Of Degenerative Spondylolisthesis. A Cadaver Study. Spine. 1980 Sep-Oct; 5(5):412-8.

Goh, J.C. et al. "Influence of PLIF cage size on lumbar spine stability." Spine. Jan. 2000, 25(1) Medline abstract (one page).

Head, W.C."Wagner surface replacement arthroplasty of the hip." Analysis of fourteen failures in forty-one hips. J Bone Joint Surg. Am; Mar. 1981, 63(3), Medline abstract (one page).

Khoo, L.T. et al. "A biomechanical analysis of the effects of lumbar fusion on the adjacent vetebral motion segment." Proceedings of the 2000 Annual Meeting of the North American Spine Society, New Orleans, pp. 127-128.

Kirkaldy-Willis, W.H. et al. "Pathology and Pathogenesis of Lumbar Spondylosis and Stenosis." Spine. Dec. 1978; 3(4):319-28.

Kotani, Y. et al. The effects of spinal fixation and destabilization on the biomechanical and histologic properties of spinal ligaments. An in vivo study. Spine, Mar. 15, 1998, 23(6), Medline abstract (2 pages).

Lemaire, J.P. et al. "Intervertebral disc prosthesis: results and prospects for the year 2000." Clinical Orthopaedics and Related Research. 1997; No. 337, pp. 64-76.

Lombardi, J.S. et al. "Treatment Of Degenerative Spondylolisthesis." Spine. 1985; 10(9): 821-7.

McMillin, C. R. et al. Artificial Spinal Discs with up to Five Years Follow-up. 20th Annual Meeting of the Society for Biomaterials (Abstract) 1994; p. 89.

Nagata, H. et al. "The effects of immobilization of long segments of the spine on the adjacent and distal facet force and lumbrosacral motion". Spine, Dec. 1993; 18(16):2471-2479, (9 pages).

Nibu, K. et al. "Multidirectional stabilizing potential of BAK interbody spinal fusion system for anterior surgery." J Spinal Discord, Aug. 1997; 10(4), Medline abstract (one page).

Posner, I. et al. A "Biomechanical Analysis of the Clinical Stability of the Lumbar and Lumbosacral Spine." Spine. 1982; 7(4): 374-389.

Rosenberg, N. J. "Degenerative Spondylolisthesis. Predisposing Factors." The Journal of Bone and Joint Surgery. 1975; 57-A(4): 467-74.

Sacher, R., Impliant Brochure for presentation at MedTech Insight Conference (Oct. 31, 2003) Boston, MA. pp. 93-94.

Szpalski, M., et al. Spine Arthroplasty: A Historical Review. Eur Spine J. 2002; 11(Suppl. 2): S65-S84.

Tsantrizos, A. et al. "Segmental stability and compressive strength of posterior lumbar interbody fusion implants." Spine, Aug. 1, 2000; 25(15), Medline abstract (one page).

UCR Pedicle Screw System from SeaSpine (information available at http://www.seaspine.com/ UCR_Pedicle_Screw_System.html). Accessed Dec. 5, 2005.

Victrex of Lancashire, Great Britain. (information on Victrex available at http://www.matweb.com). Accessed Dec. 5, 2005.

* cited by examiner

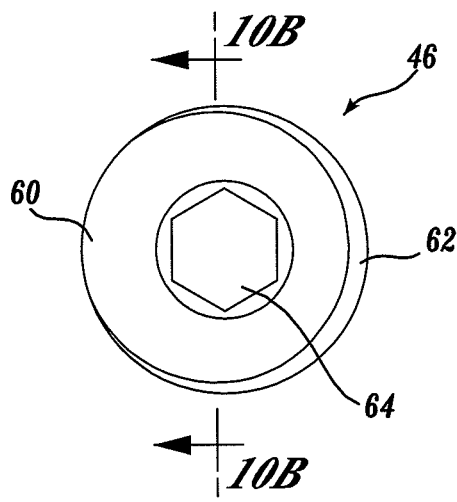
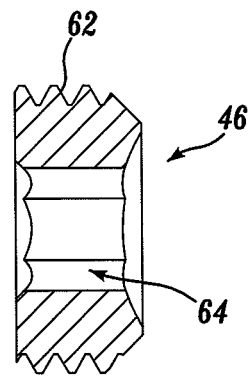
*Fig.10A.*  *Fig.10B.*
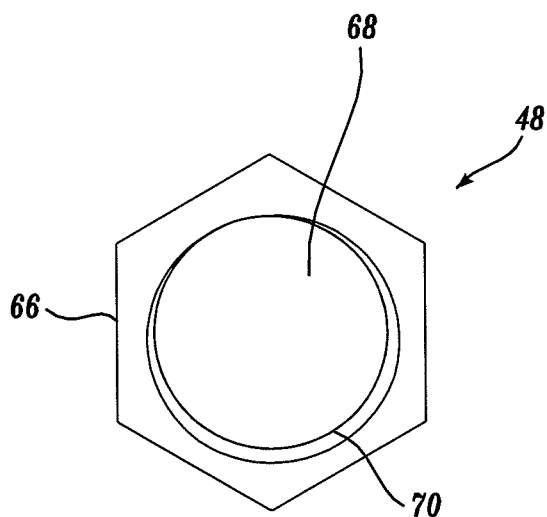
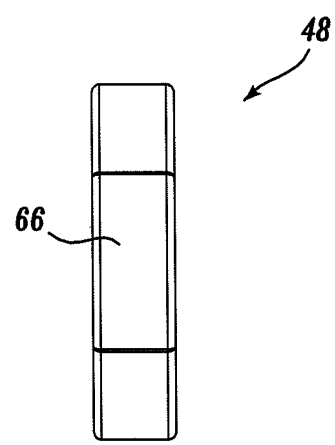
*Fig.11A.*  *Fig.11B.*

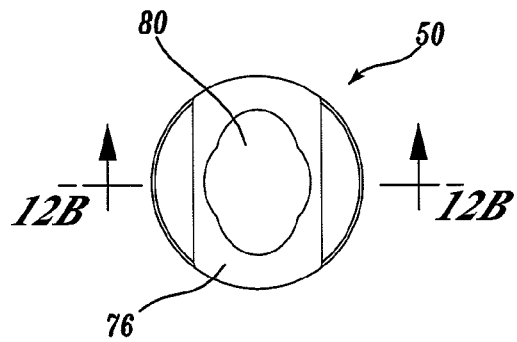
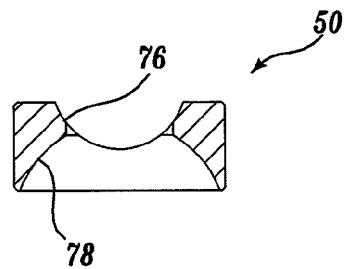
*Fig.12A.*  *Fig.12C.*
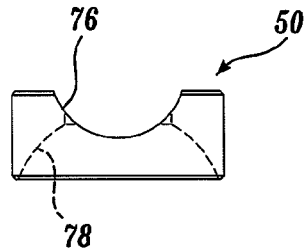
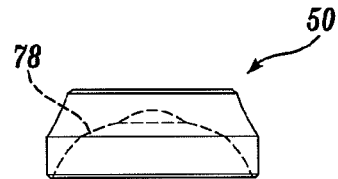
*Fig.12B.*  *Fig.12D.*
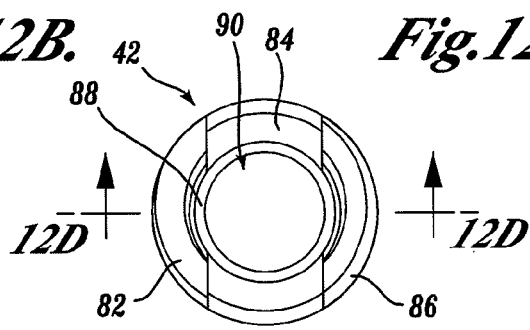
*Fig.13A.*
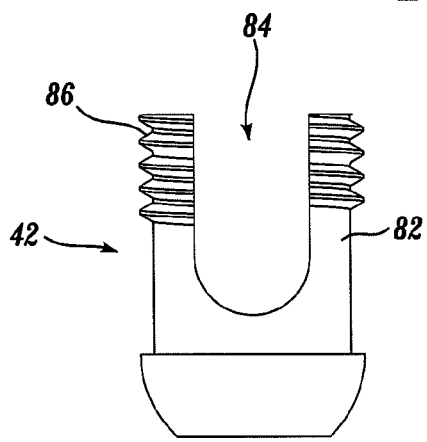
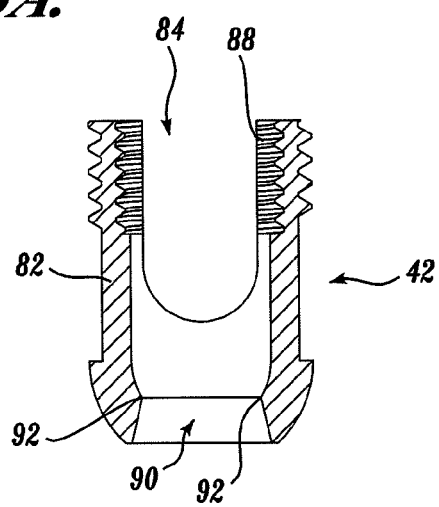
*Fig.13B.*  *Fig.13C.*

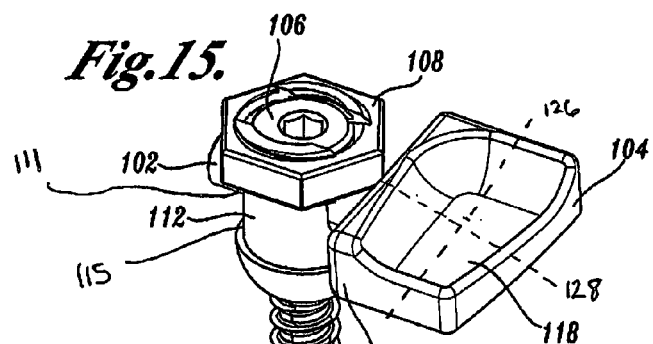
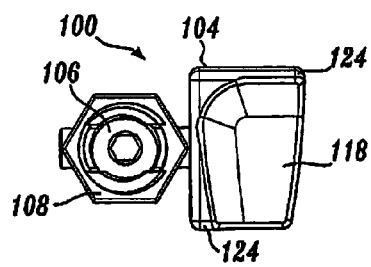
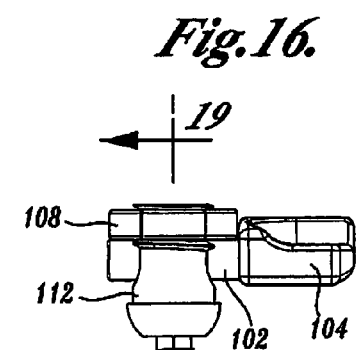
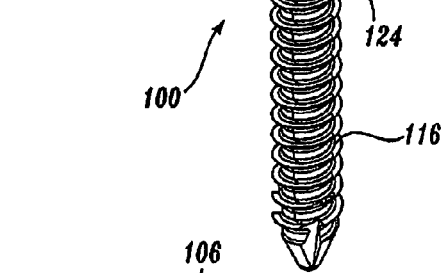
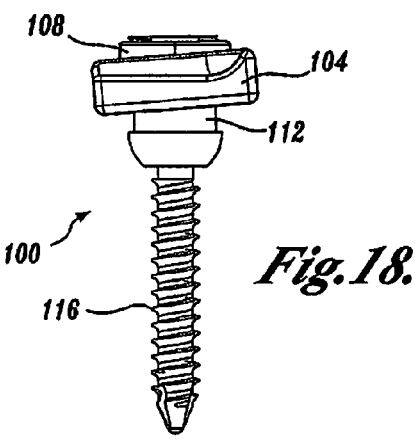
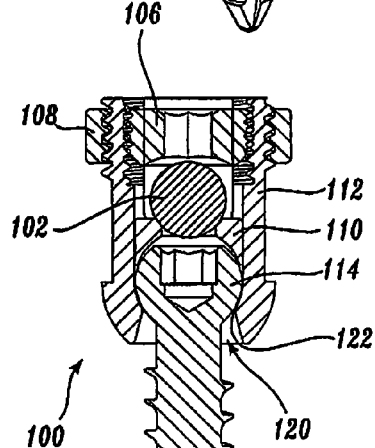
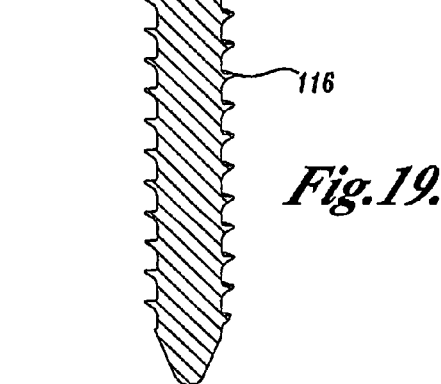

POLYAXIAL ADJUSTMENT OF FACET JOINT PROSTHESES

CROSS REFERENCE TO RELATED APPLICATIONS

This application is a continuation of U.S. application Ser. No. 10/737,705 filed on Dec. 15, 2003 entitled "Polyaxial Adjustment of Facet Joint Prostheses".

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates to prostheses, systems, and methods for treating various types of spinal pathologies, and in particular relates to attachment of prostheses to spinal vertebrae.

BACKGROUND OF THE INVENTION

The human spinal column 10, as shown in FIG. 1, is comprised of a series of thirty-three stacked vertebrae 12 divided into five regions. The cervical region includes seven vertebrae, known as C1-C7. The thoracic region includes twelve vertebrae, known as T1-T12. The lumbar region contains five vertebrae, known as L1-L5. The sacral region is comprised of five vertebrae, known as S1-S5, while the coccygeal region contains four vertebrae, known as Co1-Co4.

FIG. 2 depicts a superior plan view of a normal human lumbar vertebra 12. Although human lumbar vertebrae vary somewhat according to location, they share many common features. Each vertebra 12 includes a vertebral body 14. Two short bones, the pedicles 16, extend backward from each side of the vertebral body 14 to form a vertebral arch 18.

At the posterior end of each pedicle 16, the vertebral arch 18 flares out into broad plates of bone known as the laminae 20. The laminae 20 fuse with each other to form a spinous process 22. The spinous process 22 serves for muscle and ligamentous attachment. A smooth transition from the pedicles 16 to the laminae 20 is interrupted by the formation of a series of processes.

Two transverse processes 24 thrust out laterally on each side from the junction of the pedicle 16 with the lamina 20. The transverse processes 24 serve as levers for the attachment of muscles to the vertebrae 12. Four articular processes, two superior 26 and two inferior 28, also rise from the junctions of the pedicles 16 and the laminae 20. The superior articular processes 26 are sharp oval plates of bone rising upward on each side of the vertebrae, while the inferior processes 28 are oval plates of bone that jut downward on each side.

The superior and inferior articular processes 26 and 28 each have a natural bony structure known as a facet. The superior articular facet 30 faces upward, while the inferior articular facet 31 (see FIG. 3) faces downward. When adjacent vertebrae 12 are aligned, the facets 30 and 31, capped with a smooth articular cartilage, interlock to form a facet joint 32, also known as a zygapophyseal joint.

The facet joint 32 is composed of a superior half and an inferior half. The superior half is formed by the vertebral level below the joint 32, and the inferior half is formed by the vertebral level above the joint 32. For example, in the L4-L5 facet joint, the superior half of the joint 32 is formed by bony structure on the L5 vertebra (i.e., a superior articular surface and supporting bone 26 on the L5 vertebra), and the inferior half of the joint 32 is formed by bony structure on the L4 vertebra (i.e., an inferior articular surface and supporting bone 28 on the L4 vertebra).

An intervertebral disc 34 between each adjacent vertebrae 12 permits gliding movement between the vertebrae 12. The structure and alignment of the vertebrae 12 thus permit a range of movement of the vertebrae 12 relative to each other.

Back pain, particularly in the "small of the back" or lumbosacral (L4-S1) region, is a common ailment. In many cases, the pain severely limits a person's functional ability and quality of life. Such pain can result from a variety of spinal pathologies.

Through disease or injury, the laminae, spinous process, articular processes, or facets of one or more vertebral bodies can become damaged, such that the vertebrae no longer articulate or properly align with each other. This can result in an undesired anatomy, loss of mobility, and pain or discomfort.

For example, the vertebral facet joints can be damaged by either traumatic injury or by various disease processes. These disease processes include osteoarthritis, ankylosing spondylolysis, and degenerative spondylolisthesis. The damage to the facet joints often results in pressure on nerves, also called "pinched" nerves, or nerve compression or impingement. The result is pain, misaligned anatomy, and a corresponding loss of mobility. Pressure on nerves can also occur without facet joint pathology, e.g., a herniated disc.

One type of conventional treatment of facet joint pathology is spinal stabilization, also known as intervertebral stabilization. Intervertebral stabilization prevents relative motion between the vertebrae. By preventing movement, pain can be reduced. Stabilization can be accomplished by various methods.

One method of stabilization is spinal fusion. Another method of stabilization is fixation of any number of vertebrae to stabilize and prevent movement of the vertebrae.

Another type of conventional treatment is decompressive laminectomy. This procedure involves excision of the laminae to relieve compression of nerves.

These traditional treatments are subject to a variety of limitations and varying success rates. None of the described treatments, however, puts the spine in proper alignment or returns the spine to a desired anatomy. In addition, stabilization techniques, by holding the vertebrae in a fixed position, permanently limit a person's mobility.

There is, therefore, a need for prostheses, systems, and methods that overcome the problems and disadvantages associated with current strategies and designs in various treatments for spine pathologies, and, particularly, a need for spinal prostheses with attachment mechanisms that facilitate positioning of the prostheses when attached to the vertebrae.

SUMMARY OF THE INVENTION

The present invention provides prostheses, systems, and methods designed to replace natural facet joints and possibly part of the lamina at virtually all spinal levels including L1-L2, L2-L3, L3-L4, L4-L5, L5-S1, T11-T12, and T12-L1, using polyaxial attachment mechanisms for securing the prostheses to the vertebrae. The prostheses, systems, and methods help establish a desired anatomy to a spine and return a desired range of mobility to an individual. The prostheses, systems, and methods also help lessen or alleviate spinal pain by relieving the source nerve compression or impingement.

For the sake of description herein, the prostheses that embody features of the invention are identified as either "cephalad" or "caudal" with relation to the portion of a given natural facet joint they replace. As previously described, a natural facet joint, such as facet joint 32 (FIG. 3), has a superior half and an inferior half. In anatomical terms, the superior half of the joint is formed by the vertebral level below the joint, which can thus be called the "caudal" portion of the facet joint because it is closer to the feet of the person. The inferior half of the facet joint is formed by the vertebral level above the joint, which can thus be called the "cephalad" portion of the facet joint because it is closer to the head of the person. Thus, a prosthesis that, in use, replaces the caudal portion of a natural facet joint (i.e., the superior half) will be called a "caudal" prosthesis. Likewise, a prosthesis that, in use, replaces the cephalad portion of a natural facet joint (i.e., the inferior half) will be called a "cephalad" prosthesis.

In one aspect, the present invention provides a facet joint prosthesis including an artificial facet joint element connected to a fixation element by a polyaxially adjustable connection. In some embodiments the polyaxially adjustable connection is adapted and configured to permit the artificial facet joint element to be rotated with respect to the fixation element around more than one axis in order to tailor the prosthesis to the needs of the patient. The polyaxially adjustable connection may be further adapted and configured to permit the position of the artificial facet joint element to be continuously adjustable within an adjustability range with respect to the fixation element and may include a limit stop.

In various embodiments the artificial facet joint element is adapted to be movable medially, laterally, superiorly and/or inferiorly with respect to the fixation element. In some embodiments the polyaxially adjustable connection may be adapted and configured to permit the artificial facet joint element to be moved with respect to the fixation element after installation of the facet joint prosthesis in a patient. The invention may also include a fastener adapted and configured to prevent movement between the artificial facet joint element and the fixation element.

The artificial facet joint element in some embodiments may include a cephalad facet joint bearing surface and a cephalad facet joint bearing surface support. The cephalad facet joint bearing surface and the cephalad facet joint bearing surface support may be adapted and configured to be disposed laterally from a midline, or approximately at a midline, of a vertebra when the facet joint prosthesis is installed in a patient.

In some other embodiments the artificial facet joint element may include a caudal facet joint bearing surface and a caudal facet joint bearing surface support. The caudal facet joint bearing surface and the caudal facet joint bearing surface support may be adapted and configured to be disposed laterally from a midline of a vertebra when the facet joint prosthesis is installed in a patient.

The facet joint prosthesis may also include a longitudinally adjustable connection between the artificial facet joint element and the fixation element. For example, in embodiments where the artificial facet joint element includes a facet joint bearing surface a facet joint bearing surface support, the facet joint bearing surface support may be adapted and configured to be longitudinally movable with respect to the fixation element. The facet joint prosthesis may also include a fastener adapted and configured to prevent relative movement between the facet joint bearing surface support and the fixation element. The facet joint bearing surface support may also be further adapted and configured to be rotatable about a support longitudinal axis.

In some embodiments the polyaxially adjustable connection may include a facet joint element connection surface and a fixation element connection surface, with the facet joint element connection surface and fixation element connection surface being adapted and configured to be movable with respect to each other. In some embodiments the polyaxially adjustable connection may include a base member attached to the artificial facet joint element and movable with respect to the fixation element, and the base member may be further adapted and configured to be movable with respect to the artificial facet joint element.

Another aspect of the invention is a facet joint prosthesis including first and second artificial facet joint elements; a fixation element; and a polyaxially adjustable connection between at least one of the first or second facet joint elements and the fixation element. In some embodiments the first artificial facet joint element may include an artificial cephalad facet joint element, and the second artificial facet joint element may include an artificial caudal facet joint element. The fixation element may be a cephalad fixation element, and the polyaxially adjustable connection may include a cephalad polyaxially adjustable connection, with the facet joint prosthesis further including a caudal fixation element and a caudal polyaxially adjustable connection between the artificial caudal facet joint bearing element and the caudal fixation element. In some embodiments the artificial cephalad facet joint element includes a cephalad bearing surface and a cephalad bearing surface support, and in some embodiments the artificial caudal facet joint element comprises a caudal bearing surface and a caudal bearing surface support.

Under this aspect of the invention the first and second artificial facet joint elements may also include first and second artificial cephalad facet joint elements, respectively. The fixation element may be a first cephalad fixation element and the polyaxially adjustable connection may include a first cephalad polyaxially adjustable connection, with the facet joint prosthesis further including a second cephalad fixation element and a second cephalad polyaxially adjustable connection between the second artificial cephalad facet joint element and the second cephalad fixation element. In some embodiments the first and second artificial cephalad facet joint elements may include first second cephalad bearing surfaces, respectively. In some embodiments the first and second artificial facet joint elements may include first and second support arms, respectively, and at least one cephalad bearing surface supported by at least one of the first and second support arms. In those embodiments the cephalad bearing surface may be disposed approximately at a midline of a vertebra when the prosthesis is installed in a patient, and the prosthesis may also include an artificial caudal facet joint element comprising a caudal bearing surface adapted and configured to mate with the cephalad bearing surface. The cephalad bearing surface may also be adapted to rotate about the support arm or arms by which it is supported.

Also according to this aspect of the invention the polyaxially adjustable connection may be adapted and configured to permit at least one of the artificial facet joint elements to be rotated with respect to the fixation element around more than one axis. The polyaxially adjustable connection may also be further adapted and configured to permit the position of at least one of the artificial facet joint elements to be continuously adjustable within an adjustability range with respect to the fixation element and may include a limit stop. The polyaxially adjustable connection may also be adapted and configured to permit at least one of the artificial facet joint elements to be moved with respect to the fixation element after installation of the facet joint prosthesis in a patient. In some embodiments the facet joint prosthesis further includes a fastener adapted and configured to prevent relative movement between at least one of the artificial facet joint elements and the fixation element.

Also according to this aspect of the invention the facet joint prosthesis may further include a longitudinally adjustable connection between at least one of the artificial facet joint elements and the fixation element. In some embodiments, at least one of the artificial facet joint elements includes a facet joint bearing surface and a facet joint bearing surface support, with the facet joint bearing surface support being adapted and configured to be longitudinally movable with respect to the fixation element. The facet joint prosthesis may further include a fastener adapted and configured to prevent relative movement between the facet joint bearing surface support and the fixation element. In some embodiments the facet joint bearing surface support may be further adapted and configured to be rotatable about a support longitudinal axis.

Further according to this aspect of the invention the polyaxially adjustable connection may include a facet joint element connection surface and a fixation element connection surface, with the facet joint element connection surface and fixation element connection surface being adapted and configured to be movable with respect to each other. The polyaxially adjustable connection may include a base member attached to at least one of the artificial facet joint elements and movable with respect to the fixation element, with the base member possibly being further adapted and configured to be movable with respect to at least one of the artificial facet joint elements.

Yet another aspect of the invention provides a facet joint prosthesis including first and second fixation elements; an artificial facet joint bearing surface (such as a cephalad bearing surface) adapted and configured to be disposed approximately at a midline of a vertebra when the facet joint prosthesis is installed in a patient; and first and second polyaxially adjustable connections between the facet joint bearing surface and the first and second fixation elements, respectively. In some embodiments the first and second polyaxially adjustable connections may each be adapted and configured to permit the first and second fixation elements to be rotated with respect to the artificial facet joint bearing surface around more than one axis. The facet joint prosthesis may also further include first and second fasteners adapted and configured to prevent relative movement between the artificial facet joint bearing surface and the first and second fixation elements, respectively.

The facet joint prosthesis according to this aspect of the invention may also include first and second longitudinally adjustable connections between the artificial facet joint bearing surface and the first and second fixation elements, respectively. In some embodiments the facet joint prosthesis may include a first support arm disposed between the first fixation element and the artificial facet joint bearing surface and a second support arm disposed between the second fixation element and the artificial facet joint bearing surface, with the first and second support arms each being adapted and configured to support the artificial facet joint bearing surface and to be longitudinally movable with respect to the first and second fixation elements, respectively. The facet joint prosthesis may also further include first and second fasteners each adapted and configured to prevent relative movement between the facet joint bearing surface support and the fixation element. In some embodiments, the first support arm may be further adapted and configured to be rotatable about a first support arm longitudinal axis and the second support arm is further adapted and configured to be rotatable about a second support arm longitudinal axis. The first and second support arms may be two separate pieces, or they may be one integral piece. In some embodiments, third and fourth polyaxially adjustable connections between the facet joint bearing surface and the first and second fixation elements, respectively, may be employed.

Yet another aspect of the invention provides a facet joint prosthesis including an artificial facet joint bearing surface supported by first and second support arms adapted configured to dispose the artificial facet joint bearing surface approximately at a midline of a vertebra when the facet joint prosthesis is installed in a patient; and first and second fixation elements adapted and configured to attach the first and second support arms, respectively, to a vertebra. The first and second support arms and the artificial facet joint bearing surface may be one integral piece. In some embodiments the facet joint prosthesis further includes first and second polyaxially adjustable connections between the first and second arms and the first and second fixation elements, respectively. In some embodiments, third and fourth polyaxially adjustable connections between the facet joint bearing surface and the first and second fixation elements, respectively, may be employed.

Another aspect of the invention provides a method of installing an artificial facet joint prosthesis, where the prosthesis includes a facet joint element and a fixation element, the method including the steps of attaching the prosthesis to a vertebra with the fixation element; and adjusting positions of the facet joint element and the fixation element to a relative orientation. The adjusting step could include the step of moving the facet joint element medially, laterally, superiorly and/or inferiorly with respect to the fixation element. In some embodiments the attaching step is performed prior to the adjusting step, and in some embodiments the attaching step is performed after the adjusting step.

In some embodiments the adjusting step includes rotating the facet joint element with respect to the fixation element around more than one axis. The method may also include the step of preventing further rotation of the facet joint element after the rotating step.

In embodiments of the method where the facet joint element includes a facet joint bearing surface, the adjusting step may include the step of positioning the facet joint bearing surface laterally from a vertebra midline or approximately at a vertebra midline, and may include the step of positioning the facet joint bearing surface to face caudad or to face cephalad.

The adjusting step may also include the step of moving the facet joint element longitudinally with respect to the fixation element. In some embodiments the method may also include the step of preventing further longitudinal movement of the facet joint element after the moving step. The adjusting step may also include the step of rotating the facet joint element about a facet joint element longitudinal axis.

Other features and advantages of the invention are set forth in the following description and drawings, as well as in the appended claims.

BRIEF DESCRIPTION OF THE DRAWINGS

FIGS. 10A and 10B provide a top plan view and side section view, respectively, of the set screw shown in FIG. 9;

FIGS. 11A and 11B provide a top plan view and side elevation view, respectively, of the fixing nut shown in FIG. 9;

FIGS. 12A through 12D provide a top plan view, a front elevation view, a front section view, and a side elevation view, respectively, of the fixing insert shown in FIG. 9;

FIGS. 13A through 13C provide a top plan view, a front elevation view, and a front section view, respectively, of the base member shown in FIG. 9;

FIG. 15 is a perspective view of one embodiment of a caudal prosthesis constructed in accordance with the present invention for replacing the superior half of a natural facet joint on an inferior vertebral body;

FIG. 16 is a top plan view of the caudal prosthesis shown in FIG. 15;

FIG. 17 is a side elevation view of the caudal prosthesis shown in FIG. 15;

FIG. 18 is a front elevation view of the caudal prosthesis shown in FIG. 15;

FIG. 19 is a front section view of the caudal prosthesis shown in FIG. 15;

DETAILED DESCRIPTION OF THE PREFERRED EMBODIMENT

Figure 1:
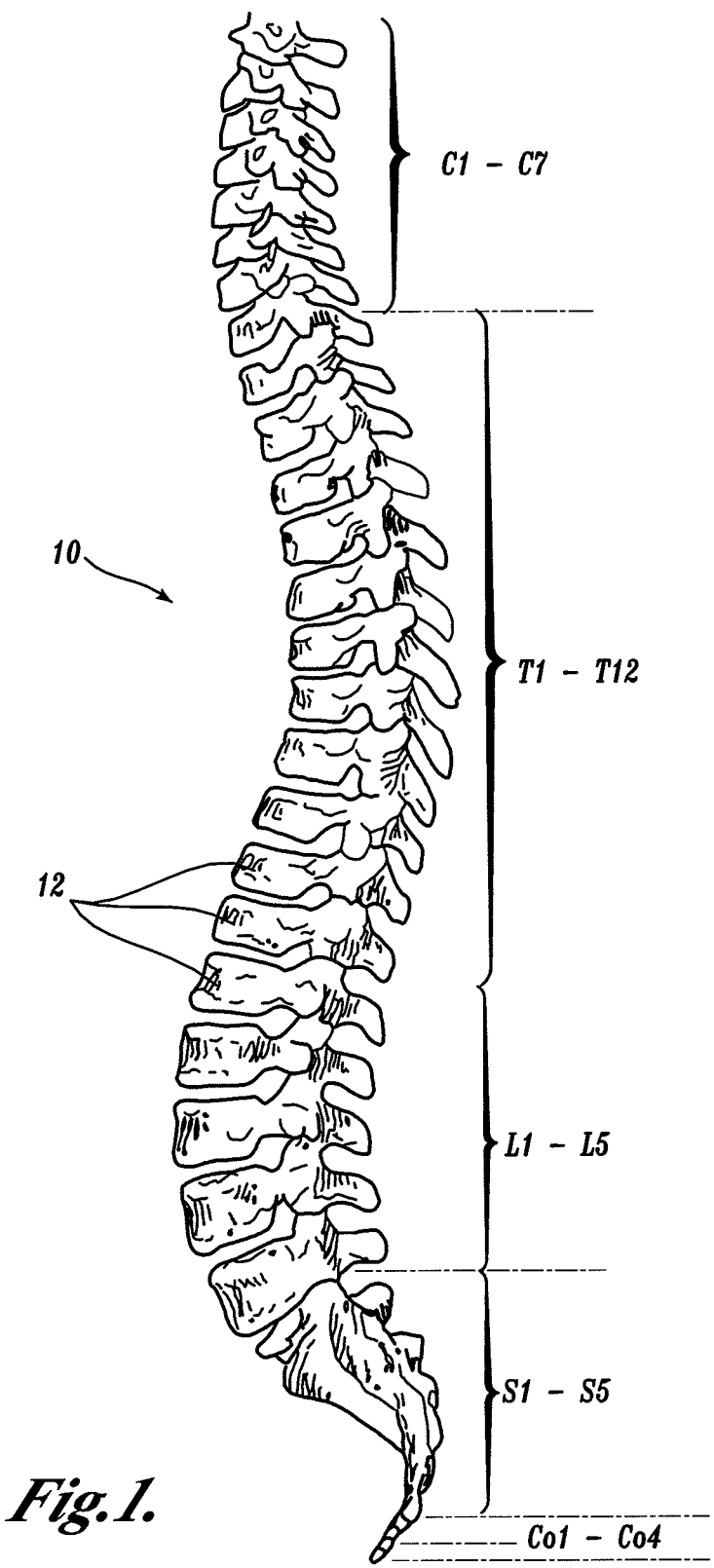
FIG. 1 is a lateral elevation view of a normal human spinal column.

Although the disclosure presented herein provides details to enable those skilled in the art to practice various embodiments of the invention, the physical embodiments disclosed herein merely exemplify the invention which may be embodied in other specific structure. Accordingly, while preferred embodiments of the invention are described below, details of the preferred embodiments may be altered without departing from the invention. All embodiments that fall within the meaning and scope of the appended claims, and equivalents thereto, are intended to be embraced by the claims.

FIGS. 4-14 show one embodiment of an artificial cephalad facet joint prosthesis 40 configured to replace the inferior portion of a natural facet joint, such as after the surgical removal of the articulating process forming the inferior portion of the facet joint. When the cephalad prosthesis 40 is attached to a vertebra, the artificial facet joint structure 44 articulates with the superior half of the facet joint 32. The superior half of the facet joint 32 can comprise the natural superior half of the facet joint (i.e., the natural superior articulating surface 30 and supporting bony structure 26) on the vertebral body below the facet joint 32. Alternatively, the superior half of the facet joint 32 may be comprised of an artificial facet joint prosthesis, such as the caudal prosthesis 100 as shown in FIGS. 15-19.

Prosthesis 40 includes an artificial facet joint element 44 connected to a fixation element 52 via a polyaxial connection 41 that permits facet joint element 44 and fixation element 52 to be rotated with respect to each other around more than one axis. As will be seen from a detailed discussion of its structure, the embodiment of FIGS. 4-14 permits continuous adjustment through relative rotation of the facet joint element and the fixation element around many different axes through an adjustability range, up to a motion limit provided by a limit stop. In other embodiments, however, the number of axes of rotation may be limited, and the movement may be permitted only in discrete increments. In various embodiments the facet joint element may be moved medially, laterally, superiorly and/or inferiorly with respect to the fixation element.

Figure 20:
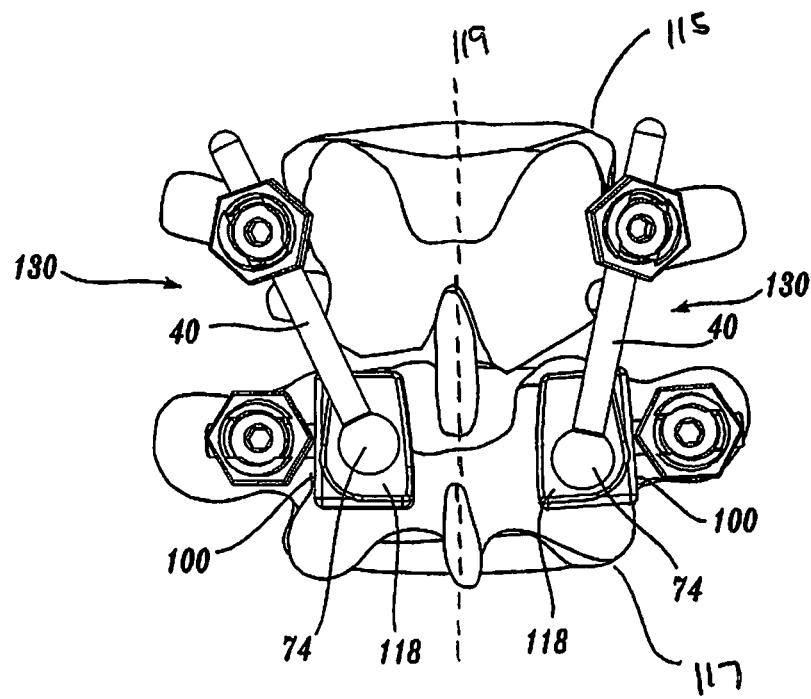
FIG. 20 is a posterior elevation view of two pairs of cephalad and caudal prostheses of this invention as installed in a patient.

The relative positions of facet joint element 44 and fixation element 52 may be set prior to implant, after implant, or both before and after implant. After implant and adjustment, the facet joint bearing surface 74 of facet joint element 44 may be in an anatomically correct position within the patient's body or in an non-anatomically correct position, depending on the requirements of the situation. For example, FIG. 20 shows facet joint prosthesis 40 implanted and adjusted to place the facet joint bearing surface 74 laterally from the midline 119 of vertebrae 115 and 117.

In alternative embodiments, other convex or concave shapes may be used for the facet joint bearing surface. Bearing surface 74 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

Fixation element 52 may be a screw, stem, corkscrew, wire, staple, adhesive, bone, and other materials known in the prosthetic arts. In the embodiment shown in FIGS. 4-14, fixation element is a screw with a head 54 and a securing portion 56. A well 58 with an outer periphery shaped to mate with a driver tool is formed in head 54. The bottom tip 57 of fixation element 52 may include cutting edges 59 that facilitate insertion of fixation element 52 into the pedicle or other portion of a vertebra.

Figure 8:
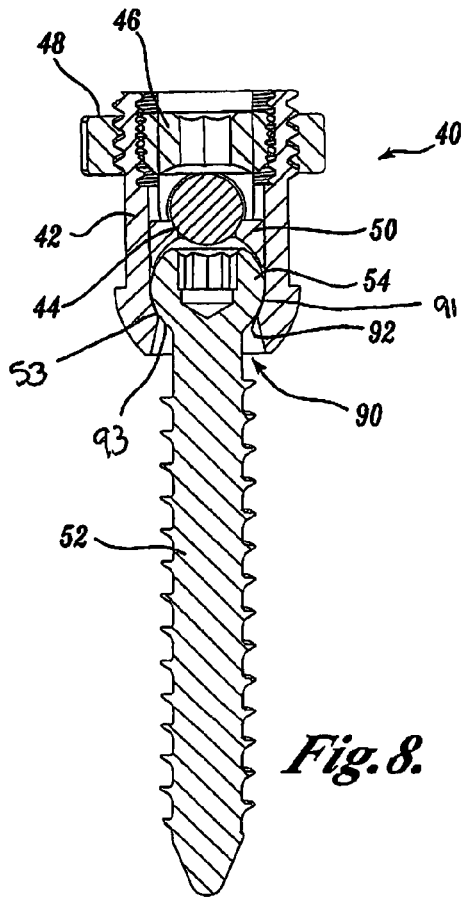
FIG. 8 is a front section view of the cephalad prosthesis shown in FIG. 4.
Figure 7:
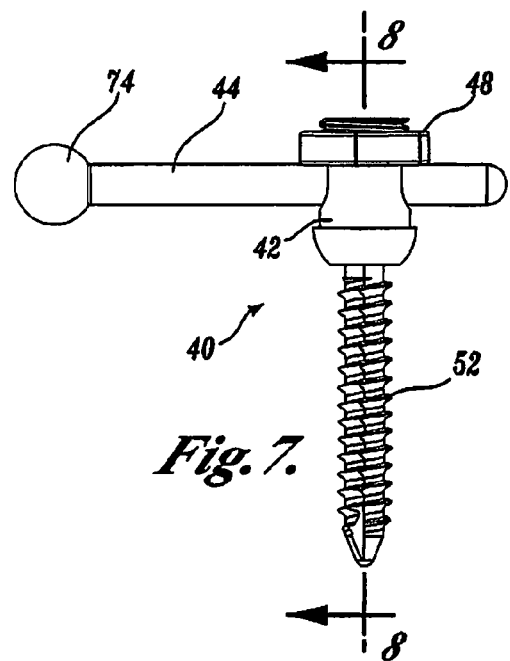
FIG. 7 is a side elevation view of the cephalad prosthesis shown in FIG. 4.
Figure 9:
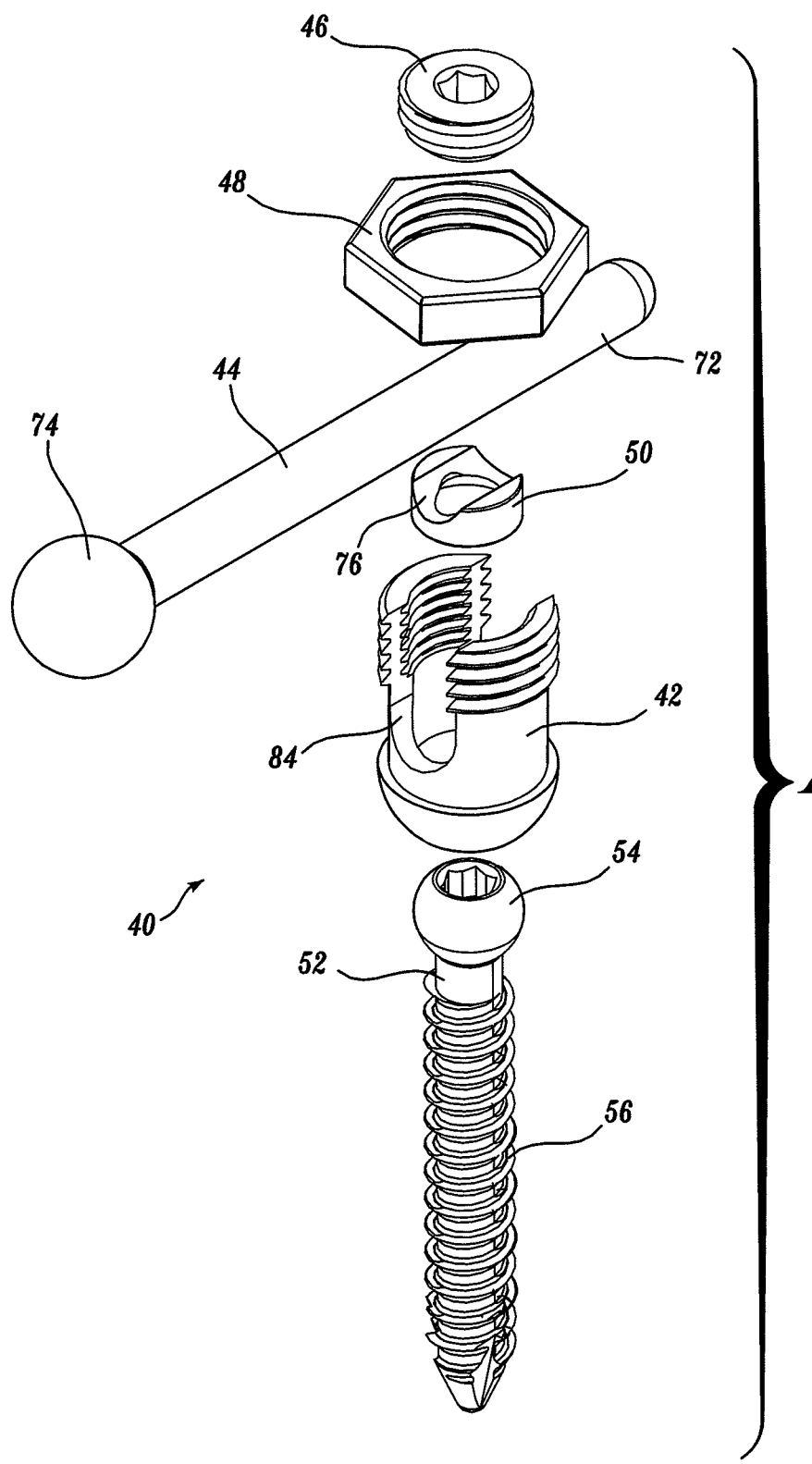
FIG. 9 is an exploded perspective view depicting various components of the cephalad prosthesis shown in FIG. 4, including a set screw, a fixing nut, an artificial facet joint structure, a fixing insert, a base member, and a polyaxial screw member.
Figure 14C:
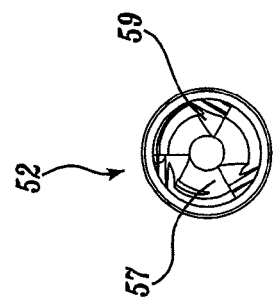
FIGS. 14A through 14D provide a side elevation view, a top plan view, a bottom plan view, and a side section view, respectively, of the polyaxial screw member shown in FIG. 9.
Figure 14A:
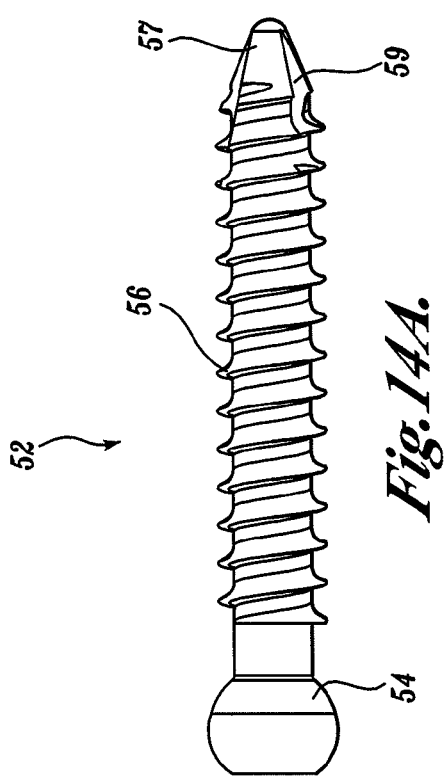
Figure 14D:
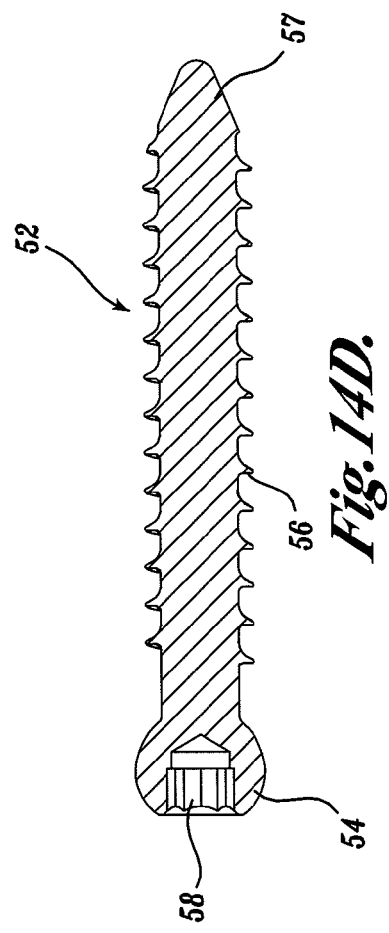
Figure 14B:
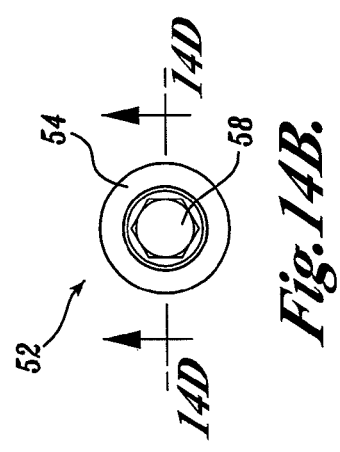

The invention may employ any suitable polyaxial connection structure, such as the structure disclosed in U.S. Pat. No. 5,360,431, the disclosure of which is incorporated by reference. In the embodiment of FIGS. 4-14, the polyaxial connection 41 of cephalad prosthesis 40 includes a base 42 connected to a support arm 72 of facet joint element 44. In alternative embodiments, base 42 may be integral with facet joint element 44. As shown in FIGS. 8, 13C and 14A, base 42 has a concave inside surface 91 that corresponds to and mates with a corresponding convex surface 53 formed on the head 54 of fixation element 52. A fixing insert 50 within base 42 also has a concave surface 78 corresponding to and mating with fixation element head 54 as shown. Concave surfaces 91 and 78 slide along convex surface 53 to permit continuous adjustment through relative rotation between facet joint element 44 and fixation element 52 along any axis desired. A limit stop surface 93 formed on the inside of base 42 interacts with fixation element 52 to limit the range of relative rotational motion between base 42 and fixation element 52 to be within an adjustability range.

In some embodiments, the facet joint prosthesis may also provide for longitudinal adjustment of the facet joint bearing surface location. For example, in the embodiment shown in FIGS. 4-14, a longitudinally adjustable connection 71 permits support arm 72 to be moved along its longitudinal axis with respect to fixation element 52. In this embodiment, longitudinally adjustable connection 71 is formed from the interaction between the rod-like support arm 72 and a U-shaped channel 76 formed on fixing insert 50. The relative positions of support arm 76 and fixation element 52 may be set prior to implant, after implant, or both before and after implant to adjust the position of the facet joint bearing surface.

Support arm 72 may also be rotated about its longitudinal axis if desired. While the embodiment shown in FIGS. 4-14 has a substantially spherical facet joint bearing surface 74, other facet joint bearing surface shapes may be used as well, and rotation of support arm 72 can help adjust the orientation of the facet joint bearing surface. Once again, the relative positions of support arm 72, facet joint bearing surface 74 and fixation element 52 may be set prior to implant, after implant, or both before and after implant.

One preferred method of installation, assembly and use of the cephalad facet joint prosthesis 40 is as follows. Fixation element 52 is inserted through the interior bore of base 42 until its head 54 rests against surface 91 of base 42. A neck 92 formed within base 42 has a diameter smaller than the diameter of head 54 to prevent fixation element 52 from passing through base 42. A driver tool (not shown) is then placed in well 58 to screw fixation element 52 into the pedicle or other portion of the vertebra. In some embodiments, an insertion hole may be formed in the vertebra prior to screwing in fixation element 52. Bone cement may also be used to hold fixation element 52 in place after insertion.

Next, the fixing insert 50 is placed within base 42 to rest on fixation element head 54. The U-shaped channel defining the upper surface 76 of the fixing insert 50 is aligned with a U-shaped opening 84 of the base member 42. Support arm 72 of the artificial facet joint element 44 is placed within the U-shaped opening 84 of base 42 and fixing insert 50.

A fixing nut 48 is threadably engaged with the outer periphery of base 42 above the artificial facet joint element 44. Similarly, a set screw 46 is threadably engaged with the inner periphery of base 42 above the artificial facet joint element 44. The center of set screw 46 is defined by an aperture 64 having a circumference shaped to mate with a corresponding driver tool (not shown).

Before the set screw 46 and fixing nut 48 are tightened, the position of base 42 is adjusted by rotating the artificial facet joint element 44, fixing insert 50 and base 42 around the outer surface of fixation element head 54. As discussed above, the sliding interaction of fixing insert 50 and base 42 with head 54 permit relative rotation of facet joint element 44 around more than one axis with respect to fixation element 52. The artificial facet joint element 44 is also adjustable along and about its longitudinal axis within base 42 to place facet joint bearing surface 74 at its desired location. When tightened, fixing nut 48 and set screw 46 act as fasteners to prevent further relative movement between artificial facet joint element 44 and fixation element 52. Other fasteners may be used, of course, as known in the art.

Figure 2:
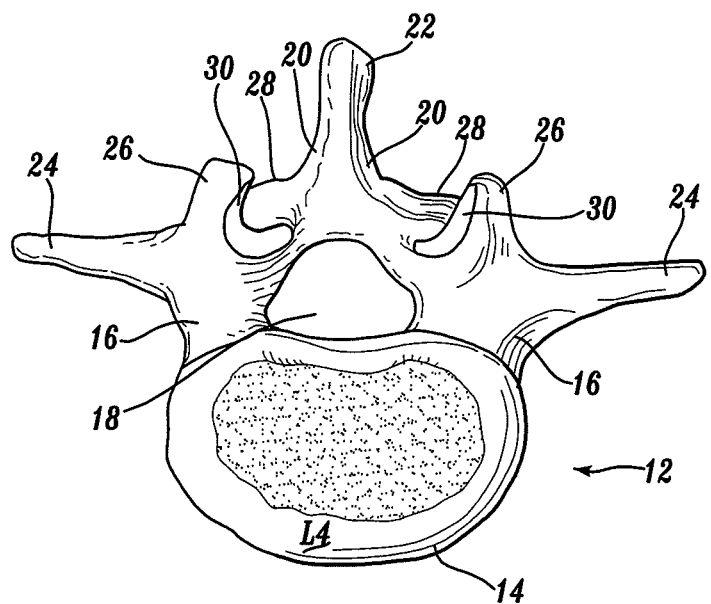
FIG. 2 is a superior plan view of a normal human lumbar vertebra.
Figure 3:
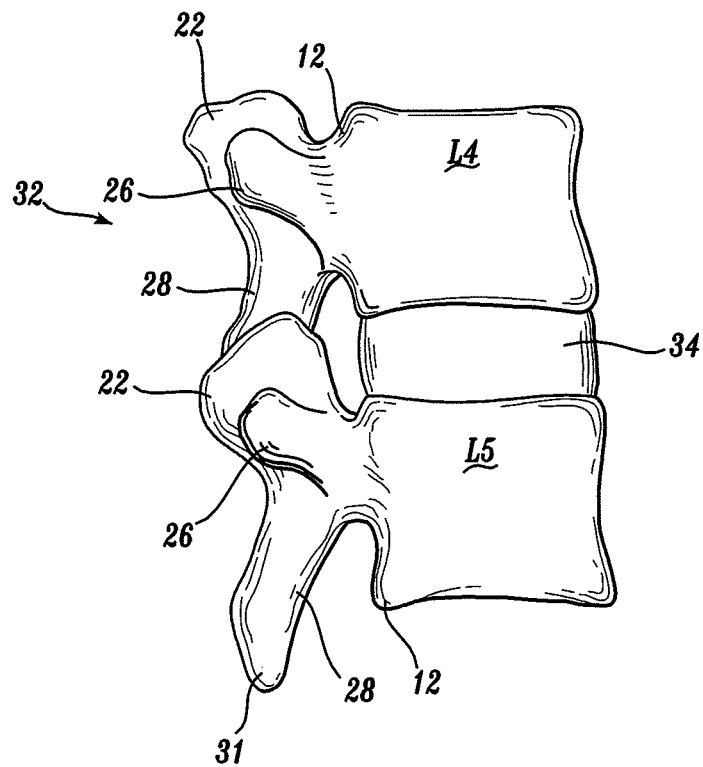
FIG. 3 is a lateral elevation view of adjoining normal human lumbar vertebrae L4 and L5.
Figure 4:
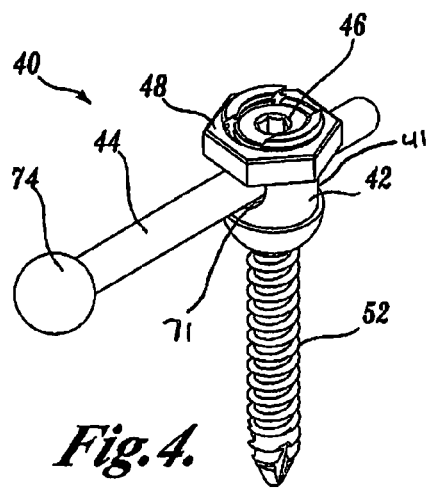
FIG. 4 is a perspective view of one embodiment of a cephalad prosthesis constructed in accordance with the present invention for replacing the inferior half of a natural facet joint on a superior vertebral body.
Figure 5:
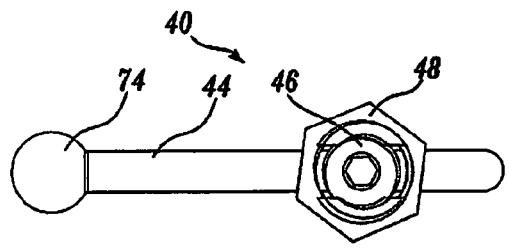
FIG. 5 is a top plan view of the cephalad prosthesis shown in FIG. 4.
Figure 6:
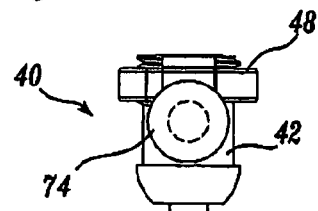
FIG. 6 is a front elevation view of the cephalad prosthesis shown in FIG. 4.

FIGS. 15-19 show one embodiment of an artificial caudal facet joint prosthesis 100 configured to replace the superior portion of a natural facet joint, such as after the surgical removal of the articulating process forming the superior portion of the facet joint. When the caudal prosthesis 100 is attached to a vertebra, the artificial facet joint structure 104 articulates with the inferior half of the facet joint. The inferior half of the facet joint can comprise the natural inferior half of the facet joint (i.e., the natural inferior articulating surface 31 and supporting bony structure 28 shown in FIGS. 2 and 3) on the vertebral body below the facet joint. Alternatively, the inferior half of the facet joint may be comprised of an artificial facet joint structure 44, such as the cephalad prosthesis shown in FIGS. 4-14.

Prosthesis 100 includes an artificial facet joint element 104 connected to a fixation element 116 via a polyaxial connection 115 that permits facet joint element 104 and fixation element 116 to be rotated with respect to each other around more than one axis. Like the embodiment shown in FIGS. 4-14, the embodiment of FIGS. 15-19 permits continuous adjustment through relative rotation of the facet joint element and the fixation element around many different axes through an adjustability range, up to a motion limit provided by a limit stop. In other embodiments, however, the number of axes of rotation may be limited, and the movement may be permitted only in discreet increments.

The relative positions of facet joint element 104 and fixation element 116 may be set prior to implant, after implant, or both before and after implant. After implant and adjustment, the facet joint bearing surface 118 of facet joint element 104 may be in an anatomically correct position within the patient's body or in an non-anatomically correct position, depending on the requirements of the situation. For example, FIG. 20 shows facet joint prosthesis 104 implanted and adjusted to place the facet joint bearing surface 118 laterally from the midline 119 of vertebrae 115 and 117.

In alternative embodiments, other convex or concave shapes may be used for the facet joint bearing surface. Bearing surface 118 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

Fixation element 116 may be a screw, stem, corkscrew, wire, staple, adhesive, bone, and other materials known in the prosthetic arts. As in the embodiment shown in FIGS. 4-14, fixation element 116 in this embodiment is a screw with a head 114 and a securing portion. A well with an outer periphery shaped to mate with a driver tool is formed in head 114, and the bottom tip of fixation element 116 may include cutting edges that facilitate insertion of fixation element 116 into the pedicle or other portion of a vertebra.

Many aspects of the caudal prosthesis of this embodiment are similar to aspects of the cephalad prosthesis described above. As shown in FIGS. 15-19, the polyaxial connection 115 of caudal prosthesis 100 includes a base 112 connected to a support arm 102 of facet joint element 104. In alternative embodiments, base 112 may be integral with facet joint element 104. Base 112 has a concave inside surface that corresponds to and mates with a corresponding convex surface formed on the head 114 of fixation element 116. A fixing insert 110 within base 112 also has a concave surface corresponding to and mating with fixation element head 114 as shown. The concave surfaces of the base and fixing insert slide along the convex surface of the fixation element head 114 to permit continuous adjustment through relative rotation between facet joint element 104 and fixation element 116 along any axis desired. A limit stop surface 120 formed on the inside of base 112 interacts with fixation element 116 to limit the range of relative rotational motion between base 112 and fixation element 116 to be within an adjustability range.

In some embodiments, the facet joint prosthesis may also provide for longitudinal adjustment of the facet joint bearing surface location. For example, in the embodiment shown in FIGS. 15-19, a longitudinally adjustable connection 111 permits support arm 102 to be moved along its longitudinal axis with respect to fixation element 116. In this embodiment, longitudinally adjustable connection 111 is formed from the interaction between the rod-like support arm 102 and a U-shaped channel formed on fixing insert 110. The relative positions of support arm 102 and fixation element 116 may be set prior to implant, after implant, or both before and after implant to adjust the position of the facet joint bearing surface.

Caudal facet joint bearing surface 118 is shaped to mate with a corresponding artificial cephalad facet joint bearing surface that is spherically shaped. In this embodiment, bearing surface 118 is generally concave with a length along one axis 126 greater than the length along a perpendicular axis 128. Other bearing surface shapes may be used, of course. Support arm 102 may be rotated about its longitudinal axis to adjust the orientation of bearing surface 118, and the relative positions of support arm 102, facet joint bearing surface 118 and fixation element 116 may be set prior to implant, after implant, or both before and after implant.

One preferred method of installation, assembly and use of the caudal facet joint prosthesis 100 is as follows. Fixation element 116 is inserted through the interior bore of base 112 until its head 114 rests against the interior surface 91 of base 112. A neck 122 formed within base 112 has a diameter smaller than the diameter of fixation element head 114 to prevent fixation element 116 from passing through base 112. A driver tool (not shown) is then used to screw fixation element 116 into the pedicle or other portion of the vertebra. In some embodiments, an insertion hole may be formed in the vertebra prior to screwing in fixation element 116. Bone cement may also be used to hold fixation element 116 in place after insertion.

Next, the fixing insert 100 is placed within base 112 to rest on fixation element head 114. A U-shaped channel in the upper surface of the fixing insert 100 is aligned with a U-shaped opening of the base member 112. Support arm 102 of the artificial facet joint element 104 is placed within the U-shaped opening of base 112 and fixing insert 100.

A fixing nut 108 is threadably engaged with the outer periphery of base 112 above the artificial facet joint element 104. Similarly, a set screw 106 is threadably engaged with the inner periphery of base 112 above the artificial facet joint element 104. The center of set screw 106 is defined by an aperture having a circumference shaped to mate with a corresponding driver tool (not shown).

Before the set screw 106 and fixing nut 108 are tightened, the position of base 112 is adjusted by rotating the artificial facet joint element 104, fixing insert 100 and base 112 around the outer surface of fixation element head 114. As discussed above, the sliding interaction of fixing insert 100 and base 112 with head 114 permit relative rotation of facet joint element 104 around more than one axis with respect to fixation element 116. The artificial facet joint element 104 is also adjustable along and about its longitudinal axis within base 112 to place facet joint bearing surface 118 at its desired location. When tightened, fixing nut 108 and set screw 106 act as fasteners to prevent further relative movement between artificial facet joint element 104 and fixation element 116. Other fasteners may be used, of course, as known in the art.

From the description herein, it should be understood that either the cephalad prosthesis 40 or the caudal prosthesis 100 may be used for unilateral facet joint replacement (one side of a given vertebral body). The prostheses 40 and 100 may also be used to provide bilateral facet joint replacement (i.e., on both the left and right sides of a given vertebral body).

Figure 21:
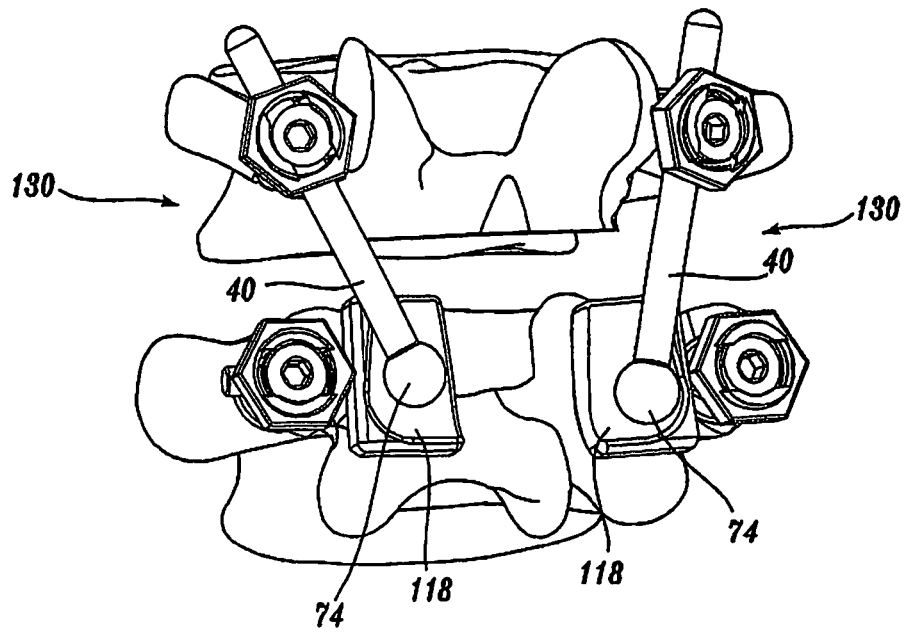
FIG. 21 is a posterior perspective view of the two pairs of installed cephalad and caudal prostheses of FIG. 20.

Furthermore, as shown in FIGS. 20 and 21, a system comprised of both prostheses 40 and 100 may be used to provide complete (i.e., superior and inferior) facet joint replacement of one or more natural facet joints. The cephalad prostheses 40 and caudal prosthesis 100 are desirably positioned to form an articulated system that replaces a natural facet joint. Cephalad prostheses 40 are attached to the superior adjoining vertebra and replace the articulating function of the cephalad portion of the natural facet joints. Likewise, caudal prostheses 100 are attached to the inferior adjoining vertebra and replace the articulating function of the caudal portion of the natural facet joints. The facet joint bearing surfaces of prostheses 40 and 100 thus cooperate to provide an artificial articular configuration. The complete facet joint replacement can be unilateral or bilateral, as desired. A bilateral facet joint replacement is shown in FIGS. 20 and 21.

FIG. 20 provides a posterior elevation view of two adjacent lumbar vertebrae after removal of the inferior and superior halves of the natural facet joints on both the left and right sides of the adjacent vertebrae. Since the inferior and superior halves of the natural facet joint are removed, the artificial articular configuration need not be constrained by, and can be unlike, the preexisting articulation of the natural facet joint prior to its removal.

Preferably, a polyaxial attachment mechanism is configured to attach either the cephalad prostheses 40 to the superior adjoining vertebra, or the caudal prostheses 100 to the inferior adjoining vertebra, or both. As described earlier, the polyaxial attachment mechanism permits the position of the artificial facet joint structure of the cephalad and/or caudal prosthesis 40, 100 (as the case may be) to be adjusted along more than one axis after the polyaxial attachment mechanism has been attached to the superior and/or inferior vertebra. The systems 130 depicted in FIGS. 20 and 21 include polyaxial attachment mechanisms for both the cephalad prostheses and the caudal prostheses. Accordingly, a physician is provided maximum flexibility to position the articulating surfaces of the prostheses 40 and 100 when the prostheses are attached to the vertebrae. The position of the artificial facet joint structures can be fully adjusted to obtain an optimal articulation between the adjoining vertebrae, and together create a desired lordotic angle between the vertebral bodies of the vertebrae.

Figure 22:
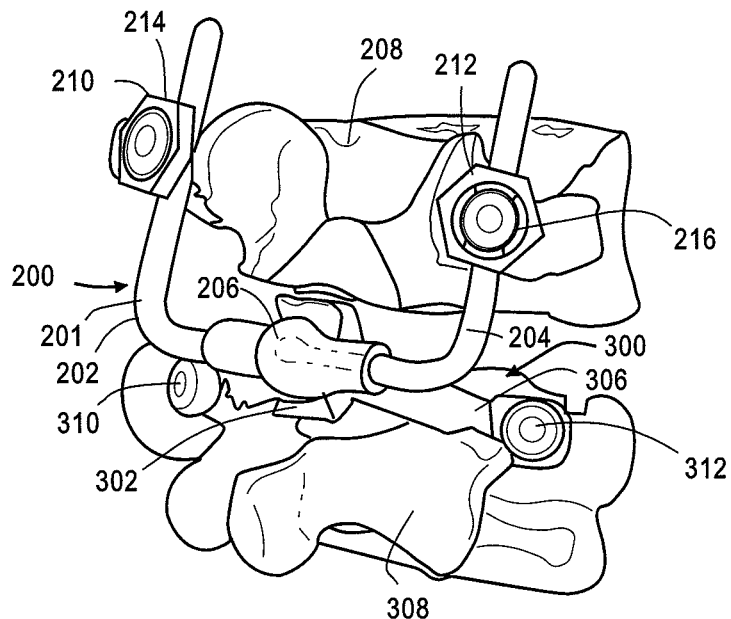
FIG. 22 is a posterior perspective view of installed cephalad and caudal prostheses according to another embodiment of the invention.
Figure 23:
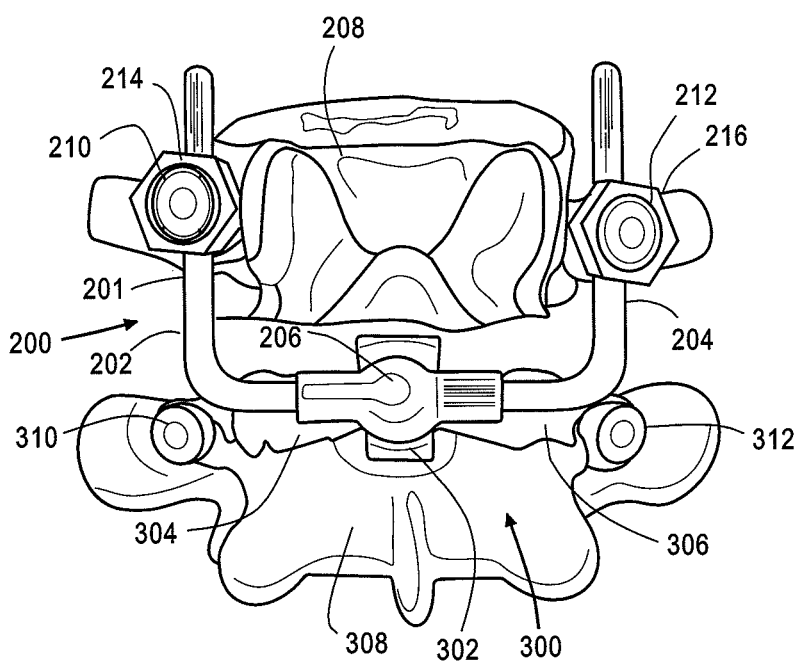
FIG. 23 is a posterior elevation view of the prostheses shown in FIG. 22.
Figure 24:
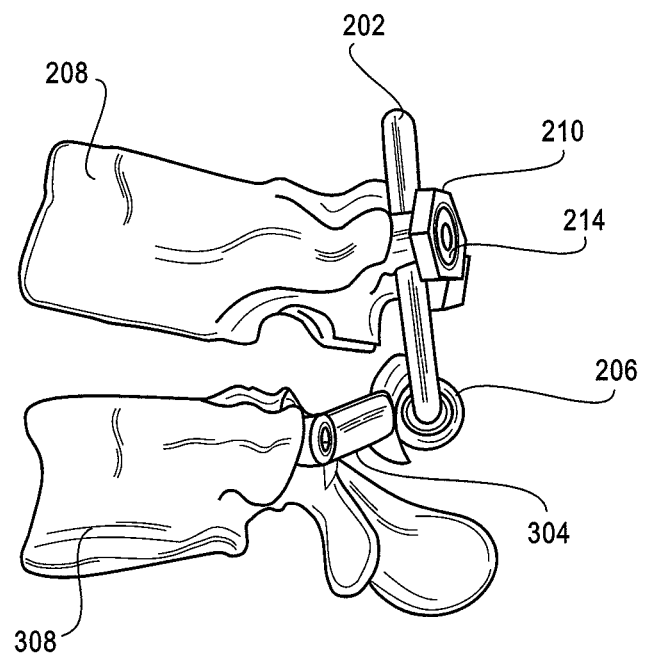
FIG. 24 is a side elevation view of the prostheses shown in FIGS. 22 and 23.
Figure 25:
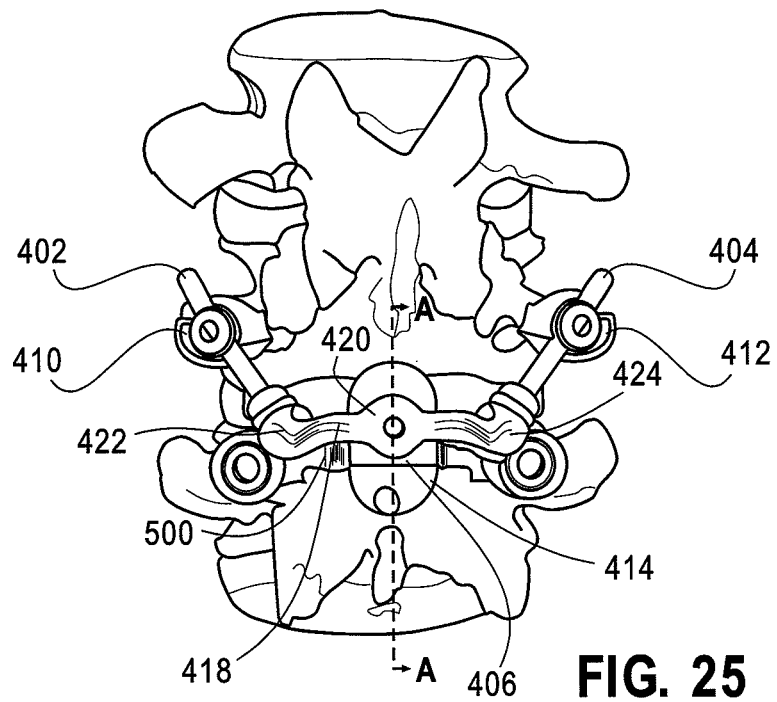
FIG. 25 is a posterior elevation view of installed cephalad and caudal prostheses according to yet another embodiment of the invention.
Figure 26:
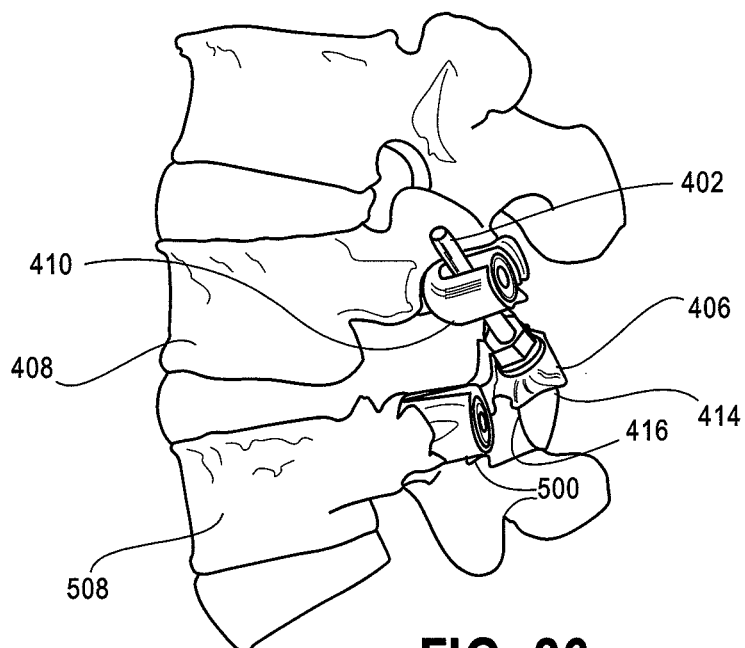
FIG. 26 is a side elevation view of the prostheses of FIG. 25.
Figure 27:
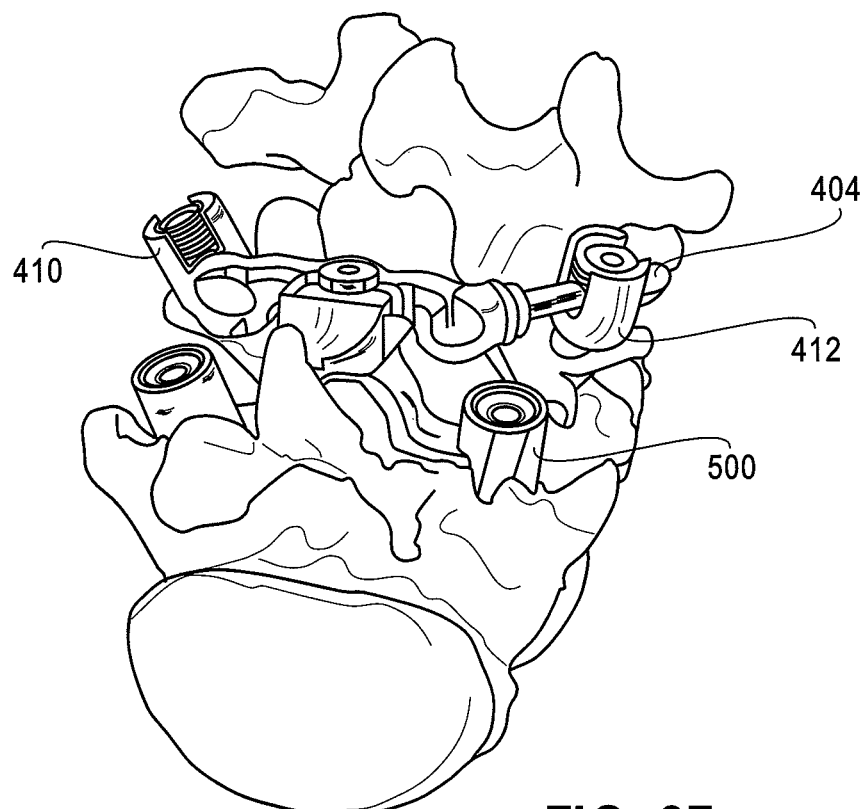
FIG. 27 is a perspective view of the prostheses of FIGS. 25 and 26.

FIGS. 22-24 show cephalad and caudal facet joint prostheses according to another embodiment of the invention providing an artificial facet joint located approximately at the center or midline of the vertebrae to which the prostheses are attached. Cephalad prosthesis 200 has a facet joint element 201 including two support arms or rods 202 and 204 supporting a cephalad bearing surface element 206. While other materials may be used, support arms 202 and 204 are preferably formed from titanium, and bearing surface element 206 is preferably formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts. In this embodiment, support arms 202 and 204 and bearing surface element 206 are separate elements and may be selected from a kit containing different size elements to meet the needs of the patient. For example, support arms ranging in size from 10 mm to 25 mm in length may be used for cephalad prostheses attached to the L4 vertebra.

In alternative embodiments, support arms 202 and 204 may be formed as a single element and may also be integral with bearing surface 206. In other alternative embodiments, one or more bushings (not shown) are disposed between bearing surface element 206 and the support arms 202 and 204 to enable bearing surface element 206 to rotate about support arms 202 and 204.

Support arms 202 and 204 are each attached to superior vertebra 208 via fixation elements such as screw, stem, corkscrew, wire, staple, adhesive, bone, and other materials known in the prosthetic arts. As shown, the fixation elements attach prosthesis 200 to pedicle portions of vertebra 208. Attachment to other portions of vertebra 208 are possible as well.

Polyaxial connections 210 and 212 between support arms 202 and 204 and their respective fixation elements permit support arms 202 and 204, and thereby cephalad facet joint element 201, to be rotated about the fixation elements around more than one axis. In fact, polyaxial connections 210 and 212 permit continuous adjustment between support arms 202 and 204 and their fixation elements around many axes, up to a motion limit provided by a limit stop. In this embodiment, polyaxial connections 210 and 212 are substantially the same as those shown in the embodiments of FIGS. 4-19. In other embodiments, however, other polyaxial connections may be used; the number of axes of rotation may also be limited, and movement may be permitted only in discrete increments.

The relative positions of cephalad facet joint element 201 and the fixation elements may be set prior to implant, after implant, or both before and after implant. In addition, this embodiment provides for longitudinal adjustment between the facet joint element 201 and the fixation elements. The longitudinally adjustable connections 214 and 216 permits arms 202 and 204, respectively, to be moved along longitudinal axes with respect to their fixation elements. Once again, the longitudinally adjustable connections of this embodiment are substantially similar to the longitudinally adjustable connections described above with respect to the embodiments shown in FIGS. 4-19. In this embodiment, support arms 202 and 204 may also be rotated about longitudinal axes, if desired. The relative longitudinal and rotational positions of support arms 202 and 204 and their fixation elements may be set prior to implant, after implant, or both before and after implant to adjust the position of the cephalad facet joint bearing surface 206.

FIGS. 22-24 also show a caudal facet joint prosthesis 300 with an artificial facet joint bearing surface 302 supported by support arms 304 and 306. In this embodiment, artificial facet bearing surface 302 is disposed substantially at the midline of vertebra 308 so as to meet and interact with the facet bearing surface 206 of cephalad prosthesis 200, as shown. Fixation elements 310 and 312 attach support arms 304 and 306, respectively, to vertebra 308, such as at pedicle portions of the vertebra. Fixation elements 310 and 312 may be a screw, stem, corkscrew, wire, staple, adhesive, bone, and other materials known in the prosthetic arts. In this embodiment, support arms 304 and 306 and facet bearing surface 302 are formed as a integral piece. In other embodiments, these elements may be formed as separate pieces. In use, caudal prosthesis 300 may be selected from a kit containing caudal prostheses of different sizes, such as between 32 mm and 60 mm wide prostheses for the L5 vertebra.

FIGS. 25-30 show yet another embodiment of the invention providing another artificial facet joint located approximately at the midline of the vertebrae. Cephalad prosthesis 400 has a facet joint element including two support arms or rods 402 and 404 supporting a cephalad bearing element 406. In this embodiment, facet joint element 406 includes a facet joint bearing surface element 414 with a facet joint bearing surface 416 formed on one side thereof. As shown, facet joint bearing surface element 414 has a plate 418 extending from its posterior side. In this embodiment, plate 418 attaches to facet joint bearing surface element 414 via a force fit connection at the crossbar's centerpoint 420. Plate 418 connects to support arms 402 and 404 via polyaxial connections 422 and 424, respectively. The appropriate size of the prosthesis, such as the width of plate 418 and the size of bearing surface 416, may be determined by a sizing tool and selected appropriately.

Support arms 402 and 404 are each attached to superior vertebra 408 via fixation elements such as screw, stem, corkscrew, wire, staple, adhesive, bone, and other materials known in the prosthetic arts. As shown, the fixation elements are screws 403 which attach prosthesis 400 to pedicle portions of vertebra 408. Attachment to other portions of vertebra 408 are possible as well.

Polyaxial connections 410 and 412 between support arms 402 and 404 and their respective fixation elements permit support arms 402 and 404, and thereby cephalad facet joint element 406, to be rotated about the pedicle fixation elements around more than one axis. In fact, polyaxial connections 410 and 412 permit continuous adjustment between support arms 402 and 404 and their fixation elements around many axes, up to a motion limit provided by a limit stop. In this embodiment, polyaxial connections 410 and 412 are substantially the same as those shown in the embodiments of FIGS. 4-19. In other embodiments, however, other polyaxial connections may be used; the number of axes of rotation may also be limited, and movement may be permitted only in discrete increments.

Figure 30:
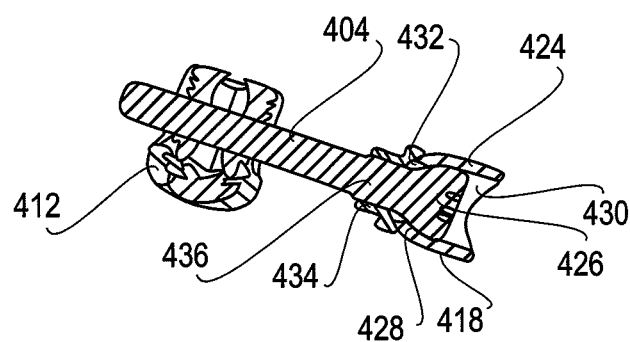
FIG. 30 is a partial sectional view taken along the line A-A shown in FIG. 29.
Figure 31:
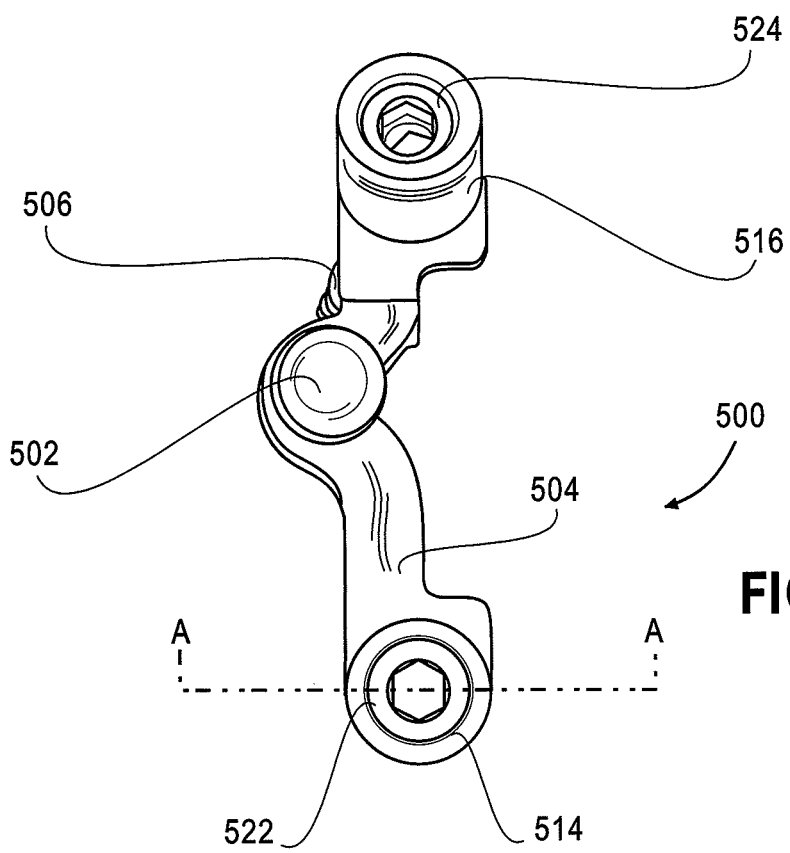
FIG. 31 is a perspective view of the caudal prosthesis of FIGS. 25-27.
Figure 32:
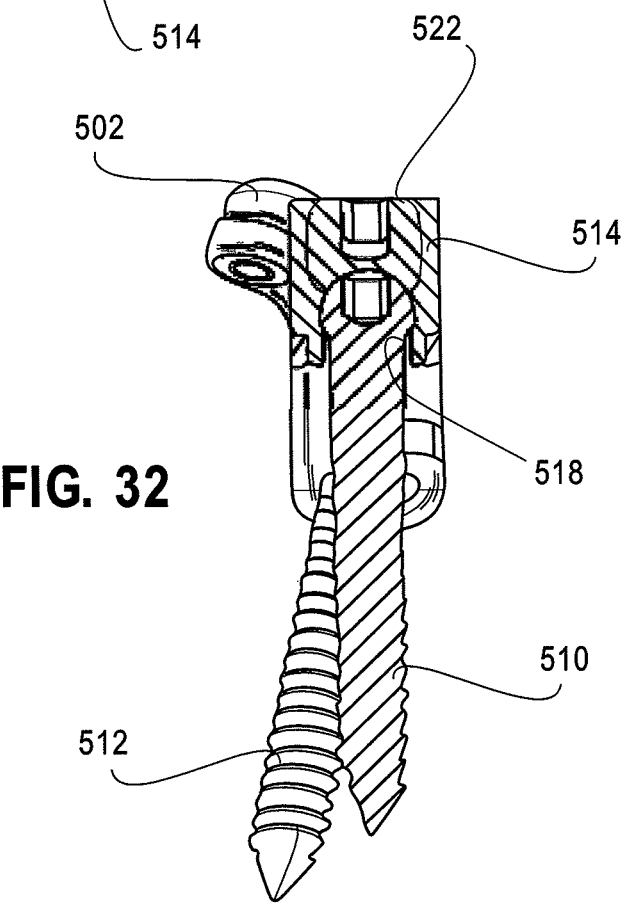
FIG. 32 is a partial sectional view taken along the line A-A shown in FIG. 31.

The structure of polyaxial connections 422 and 424 in this embodiment is shown in FIG. 30. As shown, support arm 404 has a head 426 with a substantially spherical surface 428 disposed in a spherical pocket 430 formed in plate 418. Support 404 extends through an opening 432 in plate 418 that is wider than the arm portion of support arm 404 but narrower than the support arm head 426. As can be seen from FIG. 30, the connection between support arm 404 and plate 418 permits support arm 404 and plate 418 to be rotated with respect to each other about more than one axis. Once the proper relative orientation has been achieved, a nut 434 mounted on a threaded portion 436 of support arm 404 is tightened against plate 418. The concave face of nut 434 matches the convex shape of the underside of plate 418 to enable nut 434 to be tightened against plate 418 to maintain the relative orientation of support arm 404 and plate 418. Polyaxial connection 422 has a substantially similar construction.

While other materials may be used, support arms 402 and 404 and plate 418 are preferably formed from titanium, and facet joint element 406 is preferably formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

Figure 28:
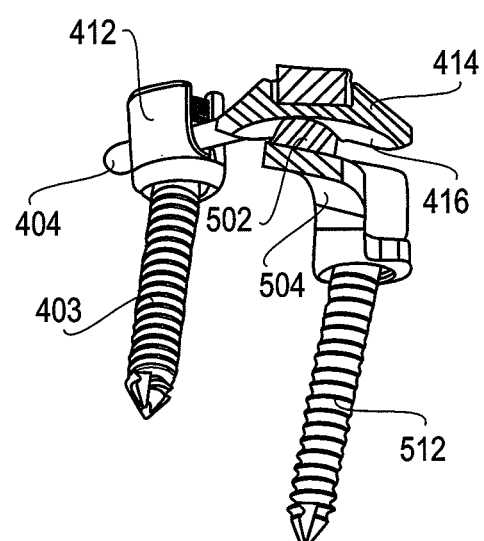
FIG. 28 is a partial sectional view taken along the line A-A shown in FIG. 25.
Figure 29:
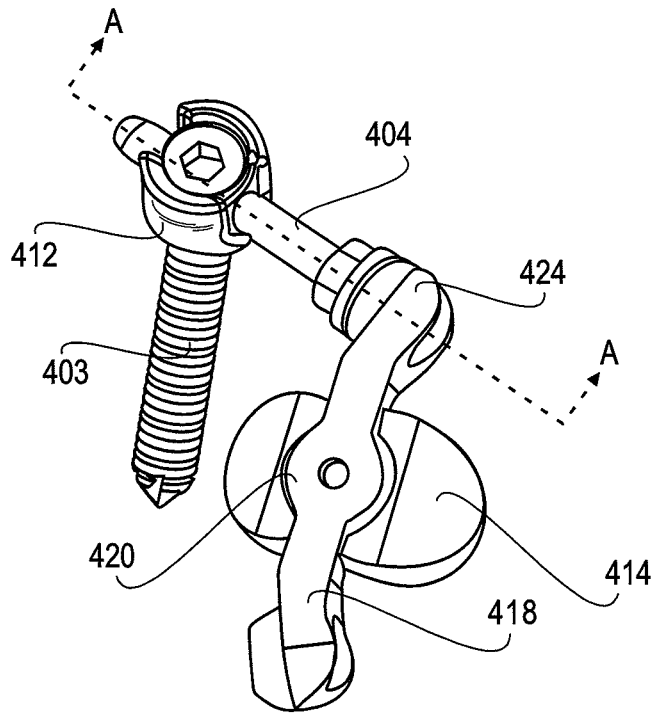
FIG. 29 is a perspective view of a portion of the cephalad prosthesis of FIGS. 25-27.

Caudal prosthesis 500 has an artificial facet joint bearing surface 502 supported by support arms 504 and 506. In this embodiment, artificial facet joint bearing surface 502 is disposed substantially at the midline of vertebra 508 so as to meet and interact with the facet joint bearing surface 416 of the cephalad prosthesis 400, as shown in FIG. 28. When installed in the patient, support arms 504 and 506 elevate facet joint bearing surface 502 above the dura portion of the vertebra.

Fixation elements 510 and 512 attach caudal prosthesis 500 to vertebra 508, such as at pedicle portions of the vertebra as shown. Fixation elements 510 and 512 may be a screw, stem, corkscrew, wire, staple, adhesive, bone, and other materials known in the prosthetic arts. In the embodiment shown in FIGS. 25-30, fixation elements 510 and 512 are self-tapping screws.

The appropriate size of caudal prosthesis 500 may be determined by using a sizing tool. To attach caudal prosthesis 500 to vertebra 508, a probe is used to determine the appropriate screw length to be used, as known in the art. The probe makes a pilot hole for the screw. As shown in FIG. 30, the screws 510 and 512 are inserted into caudal screw housings 514 and 516, respectively, which have substantially conical inside surfaces, such as surface 518 of housing 514. The screws have substantially spherical heads, such as screw head 520 of screw 510. The interaction of the spherical screw heads with the conical screw housing surfaces enables the screws to be inserted at angles other than 90°. After insertion, set screws 522 and 524 with substantially spherically concave bottom surfaces are inserted into screw housings 514 and 516, respectively, to hold support arms 504 and 506 against their respective screws.

The interaction between the cephalad and caudal bearing surfaces governs how the vertebrae to which they are attached move with respect to each other. The bearing surface shapes can provide motion limit stops and can help replace the function of removed ligaments. For example, the cephalad and caudal bearing surfaces of some preferred embodiments of the invention provide for ranges of motion of 0 to 20 degrees in flexion, 0 to 10 degrees in extension, 0 to 15 degrees in axial rotation, and 0 to 4 degrees in lateral bending.

The relative shapes of the cephalad and caudal bearing surfaces also govern the quality of the relative movement between the vertebrae to which they are attached. For example, the quality of the relative movement provided by the movable cephalad bearing surface described above with reference to FIGS. 22-24 is different than the sliding point of contact connection between the concave cephalad bearing surface and convex caudal bearing surface of the embodiment shown in FIGS. 25-30.

While preferred embodiments of the invention have been illustrated and described, it will be appreciated that various changes can be made therein without departing from the spirit and scope of the invention.

What is claimed is:

1. An apparatus comprising:
   a first spinal prosthetic member comprising a first joint element including a first support arm attachable to a first fixation element, the first support arm moveable along its longitudinal axis with respect to the first fixation element, wherein the first fixation element comprises a spherical head and wherein the first support arm is attachable to the first fixation element via a fixing element having a concave surface that rests on top of the spherical head of the first fixation element; and
   a second spinal prosthetic member comprising a second joint element including a support structure attachable to a second fixation element via a connection element and articulating with said first spinal prosthetic member to form an articulating assembly, the support structure configured to receive the first support arm, wherein the second spinal prosthetic member further comprises a set screw for locking a position of the second fixation element relative to the connection element;
   wherein the support structure is configured to receive a spherical bearing surface of the first support arm thereby allowing articulation between the first joint element and the second joint element,
   wherein the support structure includes a bearing surface that is completely enclosed by a surrounding perimeter extending from the bearing surface, the perimeter defining an opening, the opening directly opposite the bearing surface, and
   wherein the support structure is rotatable relative to the second fixation element to adjust a relative orientation of the bearing surface
   wherein the second fixation element has a first longitudinal axis and the support structure has a second longitudinal axis extending through a center of the bearing surface, wherein the support structure is offset from the second fixation element such that the second longitudinal axis does not intersect the first longitudinal axis
   wherein the second longitudinal axis is substantially parallel to the first longitudinal axis when the apparatus is implanted.

2. The apparatus according to claim 1, wherein said at least one of said first joint element or said second joint element is pivotable about a pivot.

3. The apparatus according to claim 2, wherein said at least one of said first joint element or said second joint element is fixable at a plurality of angles about the pivot.

4. The apparatus according to claim 1, wherein the support structure of the second spinal prosthetic member is attached to the second fixation element with a second support arm having a third longitudinal axis.

5. The apparatus according to claim 4, wherein the second support arm is rotatable about the third longitudinal axis to adjust the orientation of the bearing surface.

6. The apparatus according to claim 4, wherein the second support arm is movable along the third longitudinal axis with respect to the second fixation element to longitudinally adjust the bearing surface.

7. The apparatus according to claim 1, wherein at least one of the spinal prosthetic members has more than one attachment point for attaching thereto said at least one of said first or second fixation elements and said at least one of said first joint element or said second joint element is translatable from one attachment point to another.

8. The apparatus according to claim 1, wherein said at least one of said first joint element or said second joint element comprises a rounded prong.

9. The apparatus according to claim 1, wherein the first spinal prosthetic member is not rigidly affixed to the second spinal prosthetic member.

\* \* \* \* \*